(12) United States Patent
Kubota et al.

(10) Patent No.: US 9,786,846 B2
(45) Date of Patent: *Oct. 10, 2017

(54) LIGHT-EMITTING MATERIAL FOR ORGANIC ELECTROLUMINESCENT DEVICE, ORGANIC ELECTROLUMINESCENT DEVICE USING SAME, AND MATERIAL FOR ORGANIC ELECTROLUMINESCENT DEVICE

(71) Applicant: Idemitsu Kosan Co., Ltd., Tokyo (JP)

(72) Inventors: Mineyuki Kubota, Sodegaura (JP); Masakazu Funahashi, Sodegaura (JP); Chishio Hosokawa, Sodegaura (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/935,853

(22) Filed: Nov. 9, 2015

(65) Prior Publication Data

US 2016/0064675 A1   Mar. 3, 2016

Related U.S. Application Data

(60) Continuation of application No. 14/024,130, filed on Sep. 11, 2013, now Pat. No. 9,219,234, which is a division of application No. 10/583,554, filed as application No. PCT/JP2004/018964 on Dec. 13, 2004, now Pat. No. 8,853,675.

(30) Foreign Application Priority Data

Dec. 19, 2003 (JP) ................................ 2003-423317

(51) Int. Cl.
| | |
|---|---|
| H01L 51/00 | (2006.01) |
| C07C 15/28 | (2006.01) |
| C07C 15/38 | (2006.01) |
| C09K 11/06 | (2006.01) |
| H05B 33/14 | (2006.01) |
| C07C 15/60 | (2006.01) |
| H01L 51/50 | (2006.01) |

(52) U.S. Cl.
CPC .......... *H01L 51/0058* (2013.01); *C07C 15/28* (2013.01); *C07C 15/38* (2013.01); *C07C 15/60* (2013.01); *C09K 11/06* (2013.01); *H01L 51/0059* (2013.01); *H05B 33/14* (2013.01); *C07C 2603/24* (2017.05); *C07C 2603/50* (2017.05); *C09K 2211/1007* (2013.01); *C09K 2211/1011* (2013.01); *C09K 2211/1014* (2013.01); *H01L 51/5012* (2013.01); *H01L 51/5056* (2013.01)

(58) Field of Classification Search
None
See application file for complete search history.

(56) References Cited

U.S. PATENT DOCUMENTS

| | | | |
|---|---|---|---|
| 6,465,115 B2 | 10/2002 | Shi et al. | |
| 6,582,837 B1 | 6/2003 | Toguchi et al. | |
| 6,836,492 B2 | 12/2004 | Ido et al. | |
| 6,929,870 B2 | 8/2005 | Ishida et al. | |
| 8,853,675 B2* | 10/2014 | Kubota | .............. C07C 15/28 257/40 |
| 9,219,234 B2* | 12/2015 | Kubota | .............. C07C 15/28 |
| 2002/0028346 A1 | 3/2002 | Shi et al. | |
| 2002/0048687 A1 | 4/2002 | Hosokawa et al. | |
| 2003/0068524 A1 | 4/2003 | Hatwar | |
| 2004/0018380 A1 | 1/2004 | Aziz et al. | |
| 2004/0018383 A1 | 1/2004 | Aziz et al. | |
| 2005/0214565 A1 | 9/2005 | Ikeda et al. | |
| 2007/0108892 A1 | 5/2007 | Bae et al. | |

FOREIGN PATENT DOCUMENTS

| | | |
|---|---|---|
| CN | 1362464 | 8/2002 |
| CN | 1394195 | 1/2003 |
| EP | 1 009 044 A2 | 6/2000 |
| EP | 1 333 018 A1 | 8/2003 |
| EP | 1 496 041 A1 | 1/2005 |
| JP | 11-228951 | 8/1999 |
| JP | 11-323323 | 11/1999 |
| JP | 2000-182776 | 6/2000 |
| JP | 2001-097897 | 4/2001 |
| JP | 2003-086380 | 3/2003 |
| JP | 2003-146951 | 5/2003 |
| JP | 2003-313156 | 11/2003 |
| JP | 2004-059535 | 2/2004 |

OTHER PUBLICATIONS

Database WPI Week 200173, Thomson Scientific, London, GB; AN 2001-628873, XP002507806, & JP 2001 097897 A (Idemitsu Kosan Co), Apr. 10, 2001, 4 pages.
Wonhyung Lee, et al., "Synthesis and Characterization of Polyaromatic Compounds Using Tri(naphthyl)indium", J. Org. Chem. 2008, 73, 4326-4329.
JP2001-097897 Machine Translation.

* cited by examiner

*Primary Examiner* — Clinton Brooks
(74) *Attorney, Agent, or Firm* — Oblon, McClelland, Maier & Neustadt, L.L.P.

(57) ABSTRACT

Disclosed is a light-emitting material for organic electroluminescent (EL) devices which is composed of an asymmetric anthracene derivative of a specific structure. Also disclosed are a material for organic EL devices and an organic EL device wherein an organic thin film layer composed of one or more layers including at least a light-emitting layer is interposed between a cathode and an anode. At least one layer composed of the organic thin film layer contains the material for organic EL devices by itself or as a component of a mixture. Consequently, the organic EL device has a high efficiency and a long life. Also disclosed are a light-emitting material for organic EL devices and material for organic devices which enable to realize such an organic EL device.

30 Claims, No Drawings

LIGHT-EMITTING MATERIAL FOR ORGANIC ELECTROLUMINESCENT DEVICE, ORGANIC ELECTROLUMINESCENT DEVICE USING SAME, AND MATERIAL FOR ORGANIC ELECTROLUMINESCENT DEVICE

CROSS-REFERENCE TO RELATED APPLICATIONS

The present application is a continuation of U.S. Ser. No. 14/024,130, filed Sep. 11, 2013, which is a division of U.S. Ser. No. 10/583,554, filed Jun. 19, 2006, which is a National Stage of PCT/JP04/18964, filed Dec. 13, 2004, and claims priority to JP 2003-423317, filed Dec. 19, 2003.

TECHNICAL FIELD

The present invention relates to a light emitting material for an organic electroluminescence device, an organic electroluminescent device using the material and a material for an organic electroluminescent device, in particular, to an organic electroluminescence device exhibiting high current efficiency and having a long lifetime, and also to a light-emitting material for an organic electroluminescence device and a material for an organic electroluminescent device for realizing the organic EL device.

BACKGROUND ART

An organic electroluminescence ("electroluminescence" will be occasionally referred to as "EL", hereinafter) device is a spontaneous light emitting device which utilizes the principle that a fluorescent substance emits light by energy of recombination of holes injected from an anode and electrons injected from a cathode when an electric field is applied. Since an organic EL device of the laminate type driven under a low electric voltage was reported by C. W. Tang et al. of Eastman Kodak Company (C. W. Tang and S. A. Vanslyke, Applied Physics Letters, Volume 51, Pages 913, 1987), many studies have been conducted on organic EL devices using organic materials as the constituting materials.

Tang et al. used a laminate structure using tris(8-hydroxyquinolinol aluminum) for the light emitting layer and a triphenyldiamine derivative for the hole transporting layer. Advantages of the laminate structure are that the efficiency of hole injection into the light emitting layer can be increased, that the efficiency of forming excited particles which are formed by blocking and recombining electrons injected from the cathode can be increased, and that excited particles formed among the light emitting layer can be enclosed.

As the structure of the organic EL device, a two-layered structure having a hole transporting (injecting) layer and an electron transporting and light emitting layer and a three-layered structure having a hole transporting (injecting) layer, a light emitting layer and an electron transporting (injecting) layer are well known.

To increase the efficiency of recombination of injected holes and electrons in the devices of the laminate type, the structure of the device and the process for forming the device have been studied. As the light emitting material of the organic EL device, chelate complexes such as tris(8-quinolinolato)aluminum, coumarine derivatives, tetraphenylbuta diene derivatives, bisstyrylarylene derivatives and oxa diazole derivatives are known. It is reported that light in the visible region ranging from blue light to red light can be obtained by using these light emitting materials, and development of a device exhibiting color images is expected (refer to, for example, Patent literatures 1, 2 and 3).

In addition, Patent literature 4 discloses a device having phenylanthracene derivatives as a light emitting material. Although the anthracene derivatives were used as a blue light emitting material, it has been required to extend a lifetime of the device. A material having naphthyl groups at 9th and 10th positions of anthracene is disclosed in Patent literature 5 and a material having fluoranthene at 9th and 10th positions for a device is disclosed in Patent literature 6.

Although these anthracene derivatives were used as a blue light emitting material, it has been required to improve a lifetime of the device.

Further, Patent literature 7 discloses various types of anthracene derivatives to be used for a hole transporting material. However, these have not yet been evaluated as a light emitting material.

[Patent literature 1] Japanese Patent Application Laid-Open No. Heisei 8(1996)-239655

[Patent literature 2] Japanese Patent Application Laid-Open No. Heisei 7(1995)-138561

[Patent literature 3] Japanese Patent Application Laid-Open No. Heisei 3(1991)-200289

[Patent literature 4] Japanese Patent Application Laid-Open No. Heisei 8(1996)-012600

[Patent literature 5] Japanese Patent Application Laid-Open No. Heisei 11(1999)-3782

[Patent literature 6] Japanese Patent Application Laid-Open No. 2001-257074

[Patent literature 7] Japanese Patent Application Laid-Open No. 2000-182776

DISCLOSURE OF THE INVENTION

The present invention has been made to overcome the above problems and has an objective of providing an organic electroluminescence device exhibiting a great efficiency of light emission and having a long lifetime, and also to a light emitting material for realizing the organic EL device and a material for an organic electroluminescent device for realizing the organic EL device.

As a result of intensive researches and studies to achieve the above objective by the present inventors, it was found that employing a compound having a specific asymmetric anthracene structure represented by the following general formula (1) as a light emitting material of an organic EL device enables to provide the organic EL device exhibiting a great efficiency of light emission and having a long lifetime.

In other word, the present invention provides a martial for an organic EL device comprising an asymmetric anthracene derivative represented by the following general formula (1), and an organic EL device comprising at least one of organic thin film layers including a light emitting layer interposed between a pair of electrode consisting of an anode and a cathode, wherein the organic thin film layer contains at least one selected from the aforementioned asymmetric anthracene derivatives represented the general formula (1) singly or as a component of mixture thereof.

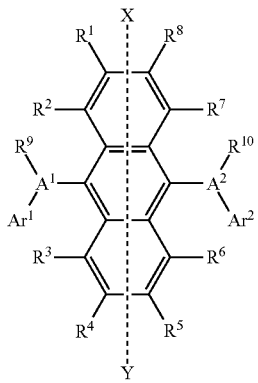

(1)

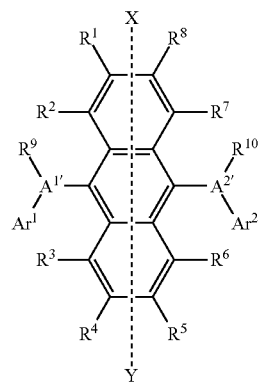

(1')

In the general formula (1), $A^1$ and $A^2$ each independently represents a substituted or unsubstituted condensed aromatic hydrocarbon ring group having ring carbon atoms of 10 to 20. $Ar^1$ and $Ar^2$ each independently represents a hydrogen atom, a substituted or unsubstituted aromatic hydrocarbon ring group having ring carbon atoms of 6 to 20. $R^1$ to $R^8$ each independently represents a hydrogen atom, a substituted or unsubstituted aromatic hydrocarbon ring group having ring carbon atoms of 6 to 50, a substituted or unsubstituted aromatic hetero ring group having ring atoms of 5 to 50, a substituted or unsubstituted alkyl group having carbon atoms of 1 to 50, a substituted or unsubstituted cycloalkyl group having carbon atoms of 3 to 50, a substituted or unsubstituted alkoxy group having carbon atoms of 1 to 50, a substituted or unsubstituted aralkyl group having carbon atoms of 6 to 50, a substituted or unsubstituted aryloxy group having carbon atoms of 5 to 50, a substituted or unsubstituted arylthio group having carbon atoms of 5 to 50, a substituted or unsubstituted alkoxycarbonyl group having carbon atoms of 1 to 50, a substituted or unsubstituted silyl group, a caboxyl group, a halogen atom, a cyano group, a nitro group or a hydroxyl group. $R^9$ to $R^{10}$ each independently represents a hydrogen atom, a substituted or unsubstituted aromatic hydrocarbon ring group having ring carbon atoms of 6 to 50, a substituted or unsubstituted alkyl group having carbon atoms of 1 to 50, a substituted or unsubstituted cycloalkyl group having carbon atoms of 3 to 50, a substituted or unsubstituted alkoxy group having carbon atoms of 1 to 50, a substituted or unsubstituted aralkyl group having carbon atoms of 6 to 50, a substituted or unsubstituted aryloxy group having carbon atoms of 5 to 50, a substituted or unsubstituted arylthio group having carbon atoms of 5 to 50, a substituted or unsubstituted alkoxycarbonyl group having carbon atoms of 1 to 50, a substituted or unsubstituted silyl group, a caboxyl group, a halogen atom, a cyano group, a nitro group or a hydroxyl group, and none of $R^9$ and $R^{10}$ is alkenyl group. $Ar^1$, $Ar^2$, $R^9$ and $R^{10}$ each may be a plural number, and two neighboring groups thereof may form a saturated or unsaturated ring structure; however, it is excluded a case where the groups at 9th and 10th positions of anthracene at the core in the general formula (1) are symmetrical at x-y axis of symmetry and bond each other.

In addition, the present invention provides a material for an organic EL device comprising an asymmetric anthracene derivative represented by the following general formula (1').

A material for an organic electroluminescent device comprising an asymmetric derivative represented by the following general formula (1').

In the general formula (1'), $A^{1'}$ and $A^{2'}$ each independently represents a substituted or unsubstituted condensed aromatic hydrocarbon ring group having ring carbon atoms of 10 to 20, and at least one of AP and $A^{2'}$ represents a naphtalene-1-yl group having a substituent at 4th position thereof or a substituted or unsubstituted condensed aromatic hydrocarbon ring group having ring carbon atoms of 12 to 20. $Ar^1$, $Ar^2$ and $R^1$ to $R^{10}$ each independently represent the same with the aforementioned; however, in the general formula (1'), it is excluded a case where the groups at 9th and 10th positions of anthracene at the core are symmetrical at x-y axis of symmetry and bond each other.

The light emitting material for an organic EL device or the organic EL device employed the asymmetric anthracene derivatives of the present invention exhibits high current efficiency and has a long lifetime.

INDUSTRIAL APPLICABILITY

As explained above in details, the light emitting material for an organic EL device or the organic EL device employed the asymmetric anthracene derivatives of the present invention represented by the general formula (1) exhibits high current efficiency and has a long lifetime. Therefore, the organic EL device is valuable for potential continuous use for a prolonged period.

THE PREFERRED EMBODIMENT TO CARRY OUT THE INVENTION

The light emitting material for an organic EL device comprises the asymmetric anthracene derivative represented by the general formula (1). It is excluded a case where the groups at 9th and 10th positions of anthracene at the core are symmetrical at x-y axis of symmetry and bond each other in the asymmetric derivatives represented by the general formula (1), which means that the general formula (1) is preferably the following structures:

(I) $A^1$ is different from $A^2$.
(II) when $A^1$ is the same with $A^2$, (II-i) $Ar^1$ is different from $Ar^2$, or (II-ii) $R^9$ is different from $R^{19}$, and
(II-iii) when $Ar^1$ and $Ar^2$ are the same with each other, and $R^9$ and $R^{10}$ are the same with each other,
(II-iii-1) the bonding position of $A^1$ to 9th position of the anthracene ring is different from the bonding position of $A^2$ to 10th position of the anthracene ring,
(II-iii-2) when both $A^1$ and $Ar^2$ are not hydrogen atoms, the bonding position of $Ar^1$ to $A^1$ is different from the bonding position of $Ar^2$ to $A^2$, and (II-iii-3) when both $R^9$ and $R^2$ are not hydrogen atoms, the bonding position of $R^9$ to $A^1$ is different from the bonding position of $R^{10}$ to $A^2$.

In the general formula (1), $A^1$ and $A^2$ each independently is a substituted or unsubstituted condensed aromatic hydrocarbon ring having ring carbon atoms of 10 to 20, preferably 10 to 16.

Examples of the substituted or unsubstituted condensed aromatic hydrocarbon ring group represented by $Ar^1$ and $Ar^2$ include 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 3-methyl-2-naphthyl group, 4-methyl-1-naphthyl group, 4-methyl-1-anthryl group and the like. Among those, 1-naphthyl group, 2-naphthyl group and 9-phenanthryl group are preferred.

In the general formula (1), $Ar^1$ and $Ar^2$ each independently represents a hydrogen atom or a substituted or unsubstituted aromatic hydrocarbon ring having ring carbon atoms of 6 to 50, preferably 6 to 16.

Examples of the substituted or unsubstituted aromatic hydrocarbon ring group represented by $A^1$ and $A^2$ include phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl) phenyl group, 3-methyl-2-naphthyl group, 4-methyl-1-naphthyl group, 4-methyl-1-anthryl group, 4'-methylbiphenylyl group, 4''-t-butyl-p-terphenyl-4-yl group and the like.

Among those, phenyl group, 1-naphthyl group, 2-naphthyl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, o-tolyl group, m-tolyl group, p-tolyl group, p-t-butylphenyl group are preferred.

In the general formula (1), $R^1$ to $R^8$ each independently represents a hydrogen atom, a substituted or unsubstituted aromatic hydrocarbon ring group having ring carbon atoms of 6 to 50, a substituted or unsubstituted aromatic hetero ring group having ring atoms of 5 to 50, a substituted or unsubstituted alkyl group having carbon atoms of 1 to 50, a substituted or unsubstituted cycloalkyl group having carbon atoms of 3 to 50, a substituted or unsubstituted alkoxy group having carbon atoms of 1 to 50, a substituted or unsubstituted aralkyl group having carbon atoms of 6 to 50, a substituted or unsubstituted aryloxy group having carbon atoms of 5 to 50, a substituted or unsubstituted arylthio group having carbon atoms of 5 to 50, a substituted or unsubstituted alkoxycarbonyl group having carbon atoms of 1 to 50, a substituted or unsubstituted silyl group, a caboxyl group, a halogen atom, a cyano group, a nitro group or a hydroxyl group.

$R^9$ to $R^{10}$ each independently represents a hydrogen atom, a substituted or unsubstituted aromatic hydrocarbon ring group having ring carbon atoms of 6 to 50, a substituted or unsubstituted alkyl group having carbon atoms of 1 to 50, a substituted or unsubstituted cycloalkyl group having carbon atoms of 3 to 50, a substituted or unsubstituted alkoxy group having carbon atoms of 1 to 50, a substituted or unsubstituted aralkyl group having carbon atoms of 6 to 50, a substituted or unsubstituted aryloxy group having carbon atoms of 5 to 50, a substituted or unsubstituted arylthio group having carbon atoms of 5 to 50, a substituted or unsubstituted alkoxycarbonyl group having carbon atoms of 1 to 50, a substituted or unsubstituted silyl group, a caboxyl group, a halogen atom, a cyano group, a nitro group or a hydroxyl group, and none of $R^9$ and $R^{10}$ is alkenyl group.

Examples of a substituted or unsubstituted aromatic hydrocarbon ring group represented by $R^1$ to $R^{10}$ include phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl) phenyl group, 3-methyl-2-naphthyl group, 4-methyl-1-naphthyl group, 4-meth yl-1-anthryl group, 4'-methylbiphenylyl group, 4''-t-butyl-p-terphenyl-4-yl group and the like.

Examples of a substituted or unsubstituted aromatic hetero ring group represented by $R^1$ to $R^8$ include 1-pyrrolyl group, 2-pyrrolyl group, 3-pyrrolyl group, pyradinyl group, 2-pyridinyl group, 3-pyridinyl group, 4-pyridinyl group, 1-indolyl group, 2-indolyl group, 3-indolyl group, 4-indolyl group, 5-indolyl group, 6-indolyl group, 7-indolyl group, 1-isoindolyl group, 2-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxanyl group, 5-quinoxanyl group, 6-quinoxanyl group, 1-carbazolyl group, 2-carbazolyl group, 3-carbazolyl group, 4-carbazolyl group, 9-carbazolyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthrolin-2-yl group, 1,7-phenanthrolin-3-yl group, 1,7-phenanthrolin-4-yl group, 1,7-phenanthrolin-5-yl group, 1,7-phenanthrolin-6-yl group, 1,7-phenanthrolin-8-yl group, 1,7-phenanthrolin-9-yl group, 1,7-phenanthrolin-10-yl group, 1,8-phenanthrolin-2-yl group, 1,8-phenanthrolin-3-yl group, 1,8-phenanthrolin-4-yl group, 1,8-phenanthrolin-5-yl group, 1,8-phenanthrolin-6-yl group, 1,8-phenanthrolin-7-yl group, 1,8-phenanthrolin-9-yl group, 1,8-phenanthrolin-10-yl group, 1,9-phenanthrolin-2-yl group, 1,9-phenanthrolin-3-yl group, 1,9-phenanthrolin-4-yl group, 1,9-phenanthrolin-5-yl group, 1,9-phenanthrolin-6-yl group, 1,9-phenanthrolin-7-yl group, 1,9-phenanthrolin-8-yl group, 1,9-phenanthrolin-10-yl group, 1,10-phenanthrolin-2-yl group, 1,10-phenanthrolin-3-yl group, 1,10-phenanthrolin-4-yl group, 1,10-phenanthrolin-5-yl group, 2,9-phenanthrolin-1-yl group, 2,9-phenanthrolin-3-yl group, 2,9-phenanthrolin-4-yl group, 2,9-phenanthrolin-5-yl group, 2,9-phenanthrolin-6-yl group, 2,9-phenanthrolin-7-yl group, 2,9-phenanthrolin-8-yl group, 2,9-phenanthrolin-10-yl group, 2,8-phenanthrolin-1-yl group, 2,8-phenanthrolin-3-yl group, 2,8-phenanthrolin-4-yl group, 2,8-phenanthrolin-5-yl group, 2,8-phenanthrolin-6-yl group, 2,8-phenanthrolin-7-yl group, 2,8-phenanthrolin-9-yl group, 2,8-phenanthrolin-10-yl group, 2,7-phenanthrolin-1-yl group, 2,7-phenanthrolin-3-yl group, 2,7-phenanthrolin-4-yl group, 2,7-phenanthrolin-5-yl group, 2,7-phenanthrolin-6-yl group, 2,7-phenanthrolin-8-yl group, 2,7-phenanthrolin-9-yl group, 2,7-phenanthrolin-10-yl group, 1-phenazinyl group, 2-phenazinyl group, 1-phenothiazinyl group, 2-phenothiazinyl group, 3-phenothiazinyl group, 4-phenothiazinyl group, 10-phenothiazinyl group, 1-phenoxazinyl group, 2-phenoxazinyl group, 3-phenoxazinyl group, 4-phenoxazinyl group, 10-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrol-1-yl group, 2-methylpyrrol-3-yl group, 2-methylpyrrol-4-yl group, 2-methylpyrrole-5-yl group, 3-methylpyrrole-1-yl group, 3-methylpyrrole-2-yl group, 3-methylpyrrole-4-yl group, 3-methylpyrrole-5-yl group, 2-t-butylpyrrole-4-yl group, 3-(2-phenylpropyl)pyrrole-1-yl group, 2-carbinyl-1-indolyl group, 4-methyl-1-indolyl group, 2-methyl-3-indolyl group, 4-methyl-3-indolyl group, 2-t-butyl-1-indolyl group, 4-t-butyl-1 indolyl group, 2-t-butyl-3-indolyl group, 4-t-butyl-3-indolyl group and the like.

Examples of a substituted or unsubstituted alkyl group represented by $R^1$ to $R^{10}$ includes methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydroxyethyl group, 1,3-dihydroxy-isopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triamino-propyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyano-propyl group, nitromethyl group, 1-nitroethyl group, 2-nitroethyl group, 2-nitroisobutyl group, 1,2-dinitroethyl group, 1,3-dinitroisopropyl group, 2,3-dinitro-t-butyl group, 1,2,3-trinitropropyl group and the like.

Examples of s substituted or unsubstituted cycloalkyl group represented by $R^1$ to $R^{10}$ include cyclopropyl group, cyclobutyl group, cyclopentyl group, cyclohexyl group, 4-methylcyclohexyl group, 1-adamanthyl group, 2-adamanthyl group, 1-norbornyl group, 2-norbornyl group and the like.

A substituted or unsubstituted alkoxy group represented by $R^1$ to $R^{10}$ is represented by —( )Y, and examples of Y include methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydroxyethyl group, 1,3-dihydroxy-isopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triamino-propyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyano-propyl group, nitromethyl group, 1-nitroethyl group, 2-nitroethyl group, 2-nitroisobutyl group, 1,2-dinitroethyl group, 1,3-dinitroisopropyl group, 2,3-dinitro-t-butyl group, 1,2,3-trinitropropyl group and the like.

Examples of a substituted or unsubstituted aralkyl group represented by $R^1$ to $R^{10}$ includes benzyl group, 1-phenylethyl group, 2-phenylethyl group, 1-phenyl-isopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, β-naphthylmethyl group, 1-β-naphthylethyl group, 2-β-naphthylethyl group, 1-β-naphthylisopropyl group, 2-β-naphthylisopropyl group, 1-pyrrolylmethyl group, 2-(1-pyrrolyl)ethyl group, p-methylbenzyl group, m-methylbenzyl group, o-methylbenzyl group, p-chlorobenzyl group, m-chlorobenzyl group, o-chlorobenzyl group, p-bromobenzyl group, m-bromobenzyl group, o-bromobenzyl group, p-iodobenzyl group, m-iodobenzyl group, o-iodobenzyl group, p-hydroxybenzyl group, m-hydroxybenzyl group, o-hydroxybenzyl group, p-aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydroxy-2-phenylisopropyl group, 1-chloro-2-phenylisopropyl group and the like. A substituted or unsubstituted aryloxy group represented by $R^1$ to $R^{10}$ is represented by —OY', and examples of Y' include phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenyl-yl group, 4"-t-butyl-p-terphenyl-4-yl group, 2-pyrrolyl group, 3-pyrrolyl group, pyradinyl group, 2-pyridinyl group, 3-pyridinyl group, 4-pyridinyl group, 1-indolyl group, 2-indolyl group, 3-indolyl group, 4-indolyl group, 5-indolyl group, 6-indolyl group, 7-indolyl group, 1-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, 2-quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxanyl group, 5-quinoxanyl group, 6-quinoxanyl group, 1-carbazolyl group, 2-carbazolyl group, 3-carbazolyl group, 4-carbazolyl group, 1-phenanthridinyl group, 2-phenanthridinyl group, 3-phenanthridinyl group, 4-phenanthridinyl group, 6-phenanthridinyl group, 7-phenanthridinylgroup, 8-phenanthridinylgroup, 9-phenanthridinylgroup, 10-phenanthridinyl group, 1-acridinyl group, 2-acridinyl group, 3-acridinyl group, 4-acridinyl group, 9-acridinyl group, 1,7-phenanthrolin-2-yl group, 1,7-phenanthrolin-3-yl group, 1,7-phenanthrolin-4-yl group, 1,7-phenanthrolin-5-yl group, 1,7-phenanthrolin-6-yl group, 1,7-phenanthrolin-8-yl group, 1,7-phenanthrolin-9-yl group, 1,7-phenanthrolin-10-yl group, 1,8-phenanthrolin-2-yl group, 1,8-phenanthrolin-3-yl group, 1,8-phenanthrolin-4-yl group, 1,8-phenanthrolin-5-yl group, 1,8-phenanthrolin-6-yl group, 1,8-phenanthrolin-7-yl group, 1,8-phenanthrolin-9-yl group, 1,8-phenanthrolin-10-yl group, 1,9-phenanthrolin-2-yl group, 1,9-phenanthrolin-3-yl group, 1,9-phenanthrolin-4-yl group, 1,9-phenanthrolin-5-yl group, 1,9-phenanthrolin-6-yl group, 1,9-phenanthrolin-7-yl group, 1,9-phenanthrolin-8-yl group, 1,9-phenanthrolin-10-yl group, 1,10-phenanthrolin-2-yl group, 1,10-phenanthrolin-3-yl group, 1,10-phenanthrolin-4-yl group, 1,10-phenanthrolin-5-yl group, 2,9-phenanthrolin-1-yl group, 2,9-phenanthrolin-3-yl group, 2,9-phenanthrolin-4-yl group, 2,9-phenanthrolin-5-yl group, 2,9-phenanthrolin-6-yl group, 2,9-phenanthrolin-7-yl group, 2,9-phenanthrolin-8-yl group, 2,9-phenanthrolin-10-yl group, 2,8-phenanthrolin-1-yl group, 2,8-phenanthrolin-3-yl group, 2,8-phenanthrolin-4-yl group, 2,8-phenanthrolin-5-yl group, 2,8-phenanthrolin-6-yl group, 2,8-phenanthrolin-7-yl group, 2,8-phenanthrolin-9-yl group, 2,8-phenanthrolin-10-yl group, 2,7-phenanthrolin-1-yl group, 2,7-phenanthrolin-3-yl group, 2,7-phenanthrolin-4-yl group, 2,7-phenanthrolin-5-yl group, 2,7-phenanthrolin-6-yl group, 2,7-phenanthrolin-8-yl group, 2,7-phenanthrolin-9-yl group, 2,7-phenanthrolin-10-yl group, 1-phenazinyl group, 2-phenazinyl group, 1-phenothiazinyl group, 2-phenothiazinyl group, 3-phenothiazinyl group, 4-phenothiazinyl group, 1-phenoxazinyl group, 2-phenoxazinyl group, 3-phenoxazinyl group, 4-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrol-1-yl group, 2-methylpyrrol-3-yl group, 2-methylpyrrol-4-yl group, 2-methylpyrrole-5-yl group, 3-methylpyrrole-1-yl group, 3-methylpyrrole-2-yl group, 3-methylpyrrole-4-yl group, 3-methylpyrrole-5-yl group, 2-t-butylpyrrole-4-yl group, 3-(2-phenylpropyl)pyrrole-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group, 4-t-butyl-3-indolyl group and the like.

A substituted or unsubstituted arylthio group represented by $R^1$ to $R^{10}$ is represented by —SY", and examples of Y" include phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl) phenyl group, 3-methyl-2-naphthyl group, 4-methyl-1-naphthyl group, 4-methyl-1-anthryl group, 4'-methylbiphenyl-yl group, 4''-t-butyl-p-terphenyl-4-yl group, 2-pyrrolyl group, 3-pyrrolyl group, pyradinyl group, 2-pyridinyl group, 3-pyridinyl group, 4-pyridinyl group, 1-indolyl group, 2-indolyl group, 3-indolyl group, 4-indolyl group, 5-indolyl group, 6-indolyl group, 7-indolyl group, 1-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, 2-quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxanyl group, 5-quinoxanyl group, 6-quinoxanyl group, 1-carbazolyl group, 2-carbazolyl group, 3-carbazolyl group, 4-carbazolyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthrolin-2-yl group, 1,7-phenanthrolin-3-yl group, 1,7-phenanthrolin-4-yl group, 1,7-phenanthrolin-5-yl group, 1,7-phenanthrolin-6-yl group, 1,7-phenanthrolin-8-yl group, 1,7-phenanthrolin-9-yl group, 1,7-phenanthrolin-10-yl group, 1,8-phenanthrolin-2-yl group, 1,8-phenanthrolin-3-yl group, 1,8-phenanthrolin-4-yl group, 1,8-phenanthrolin-5-yl group, 1,8-phenanthrolin-6-yl group, 1,8-phenanthrolin-7-yl group, 1,8-phenanthrolin-9-yl group, 1,8-phenanthrolin-10-yl group, 1,9-phenanthrolin-2-yl group, 1,9-phenanthrolin-3-yl group, 1,9-phenanthrolin-4-yl group, 1,9-phenanthrolin-5-yl group, 1,9-phenanthrolin-6-yl group, 1,9-phenanthrolin-7-yl group, 1,9-phenanthrolin-8-yl group, 1,9-phenanthrolin-10-yl group, 1,10-phenanthrolin-2-yl group, 1,10-phenanthrolin-3-yl group, 1,10-phenanthrolin-4-yl group, 1,10-phenanthrolin-5-yl group, 2,9-phenanthrolin-1-yl group, 2,9-phenanthrolin-3-yl group, 2,9-phenanthrolin-4-yl group, 2,9-phenanthrolin-5-yl group, 2,9-phenanthrolin-6-yl group, 2,9-phenanthrolin-7-yl group, 2,9-phenanthrolin-8-yl group, 2,9-phenanthrolin-10-yl group, 2,8-phenanthrolin-1-yl group, 2,8-phenanthrolin-3-yl group, 2,8-phenanthrolin-4-yl group, 2,8-phenanthrolin-5-yl group, 2,8-phenanthrolin-6-yl group, 2,8-phenanthrolin-7-yl group, 2,8-phenanthrolin-9-yl group, 2,8-phenanthrolin-10-yl group, 2,7-phenanthrolin-1- yl group, 2,7-phenanthrolin-3-yl group, 2,7-phenanthrolin-4-yl group, 2,7-phenanthrolin-5-yl group, 2,7-phenanthrolin-6-yl group, 2,7-phenanthrolin-8-yl group, 2,7-phenanthrolin-9-yl group, 2,7-phenanthrolin-10-yl group, 1-phenazinyl group, 2-phenazinyl group, 1-phenothiazinyl group, 2-phenothiazinyl group, 3-phenothiazinyl group, 4-phenothiazinyl group, 1-phenoxazinyl group, 2-phenoxazinyl group, 3-phenoxazinyl group, 4-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrol-1-yl group, 2-methylpyrrol-3-yl group, 2-methylpyrrol-4-yl group, 2-methylpyrrole-5-yl group, 3-methylpyrrole-1-yl group, 3-methylpyrrole-2-yl group, 3-methylpyrrole-4-yl group, 3-methylpyrrole-5-yl group, 2-t-butylpyrrole-4-yl group, 3-(2-phenylpropyl)pyrrole-1-yl group, 2-methyl-1-indolyl group, 4-methyl-1-indolyl group, 2-methyl-3-indolyl group, 4-methyl-3-indolyl group, 2-t-butyl 1-indolyl group, 4-t-butyl 1-indolyl group, 2-t-butyl 3-indolyl group, 4-t-butyl 3-indolyl group and the like.

A substituted or unsubstituted alkoxycarbonyl group for $R^1$ to $R^{10}$ is represented by —COOZ, and examples of Z include methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydroxyethyl group, 1,3-dihydroxy-isopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triamino-propyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyano-propyl group, nitromethyl group, 1-nitroethyl group, 2-nitroethyl group, 2-nitroisobutyl group, 1,2-dinitroethyl group, 1,3-dinitroisopropyl group, 2,3-dinitro-t-butyl group, 1,2,3-trinitropropyl group and the like.

Examples of a halogen atom for $R^1$ to $R^{10}$ include fluorine atom, chlorine atom, bromine atom and the like A substituent for the $Ar^1$, $Ar^2$ and $R^1$ to $R^{10}$ includes halogen atom, hydroxyl group, nitro group, cyano group, alkyl group, aryl group, cycloalkyl group, alkoxy group, aralkyl group, aryloxy group, arylthio group, alkoxycarbonyl group, carboxyl group or the like.

$Ar^1$, $Ar^2$, $R^9$ and $R^{10}$ each may be a plural number, and two neighboring groups thereof may form a saturated or unsaturated ring structure, and the ring structure includes, in addition to unsaturated 6 member ring such as benzene, saturated or unsaturated 5 member or 7 member ring structure and the like.

Further, in the present invention, it is preferable that the asymmetric anthracene derivatives represented by the aforementioned general formula (1) comprise a naphthalene-1-yl group having substituent at 4th position thereof and/or a substituted or unsubstituted condensed aromatic hydrocarbon ring having ring carbon atoms of 12 to 20. Examples of the substituent includes the same with the substituent of the groups represented by $Ar^1$, $Ar^2$ and $R^1$ to $R^{10}$ The material for the organic EL device of the present invention comprises the asymmetric anthracene derivatives represented by the aforementioned general formula (1'). The general formula (1') is shown by that $A^{1'}$ and $A^{2'}$ each independently are limited to a substituted or unsubstituted condensed aromatic hydrocarbon ring having ring carbon atoms of 10 to 20, and at least one of $A^{1'}$ and $A^{2'}$ is limited to naphthalene-1-yl group having substituent at 4th position thereof or a substituted or unsubstituted condensed aromatic hydrocarbon ring having ring carbon atoms of 12 to 20. $Ar^1$, $Ar^2$ and $R^1$ to $R^{10}$ each independently is the same with aforementioned so that examples of each group thereof and preferable groups, and examples of the substituent are the same with aforementioned.

In addition, as mentioned in the general formula (1), it is excluded a case where the groups at 9th and 10th positions of anthracene at the core in the general formula (1') are symmetrical at x-y axis of symmetry and bond each other.

As the general formula (1) includes the general formula (1'), the general formula (1') is included in the general formula (1) when it is called simply "the general formula (1)".

Specific examples of the asymmetric anthracene of the present invention represented by the general formula (1) include as follows, but not limited thereto:

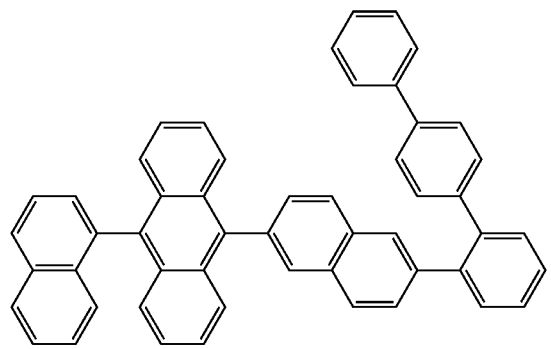

AN1

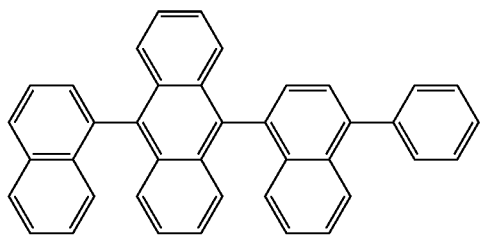

AN2

-continued
AN3
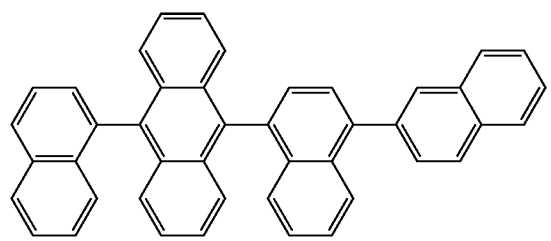
AN4
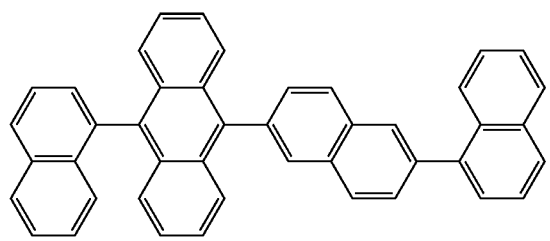
AN5
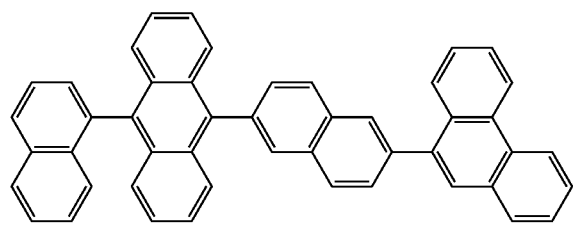
AN6
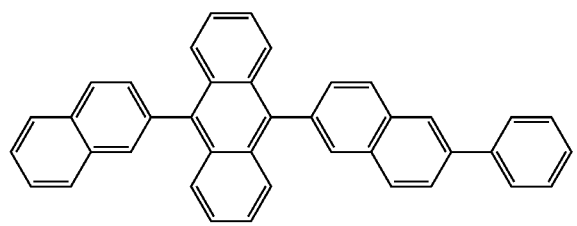
AN7
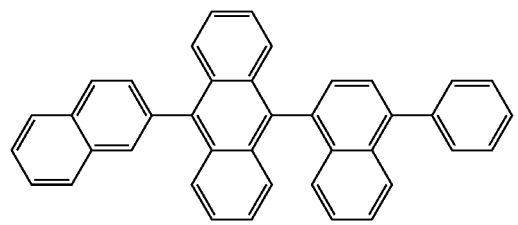
AN8
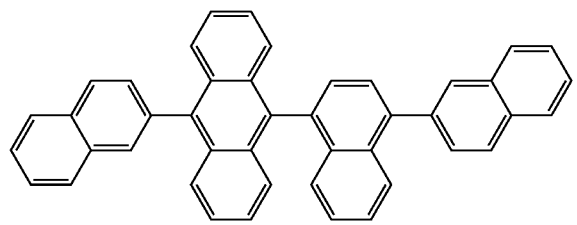
AN9
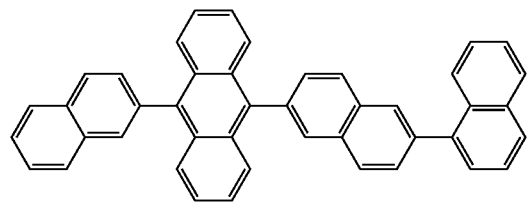
AN10
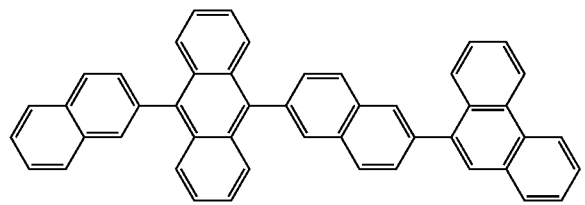
AN11
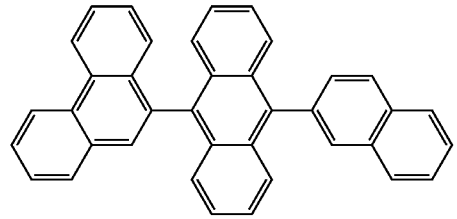
AN12
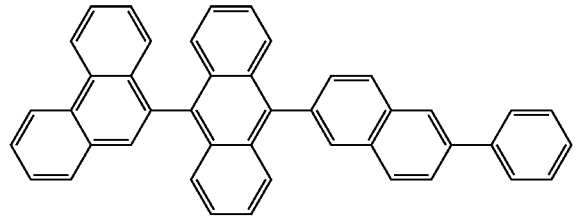
AN13
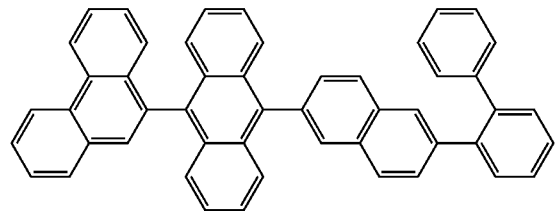
AN14
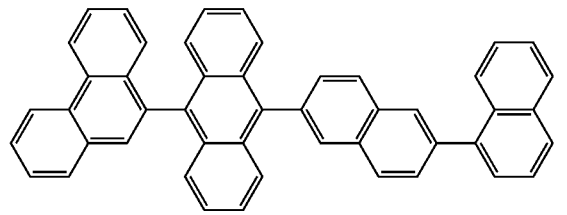

-continued
AN15
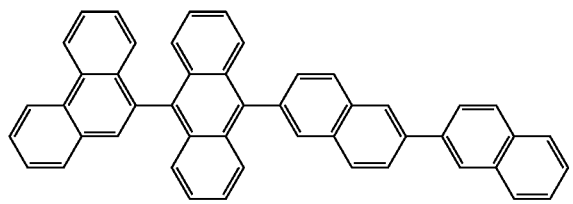
AN16
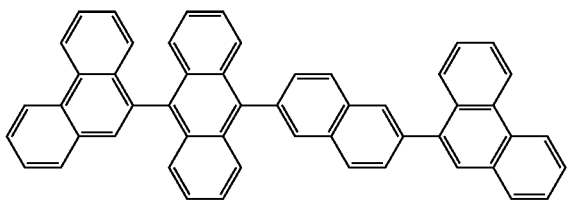
AN17
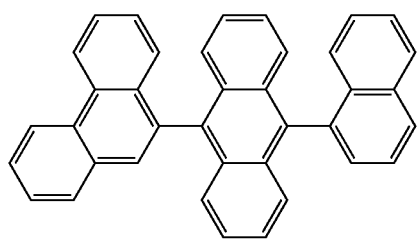
AN18
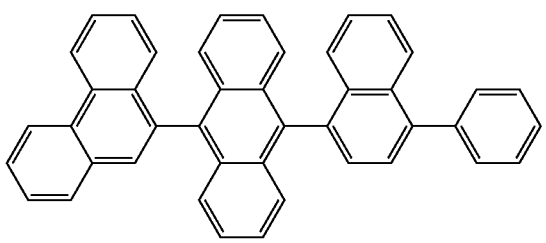
AN19
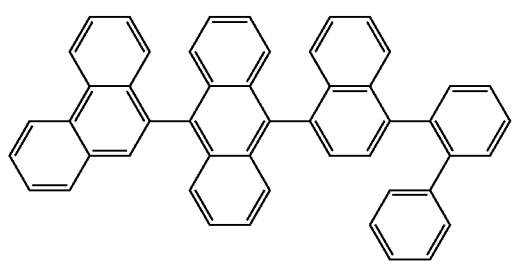
AN20
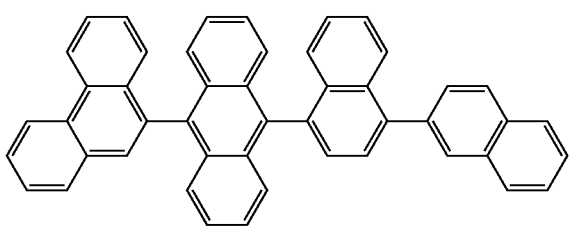
AN21
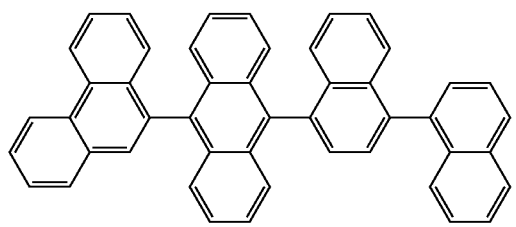
AN22
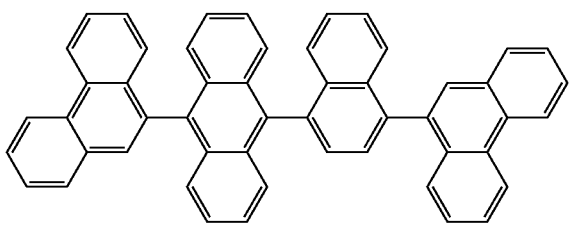
AN23
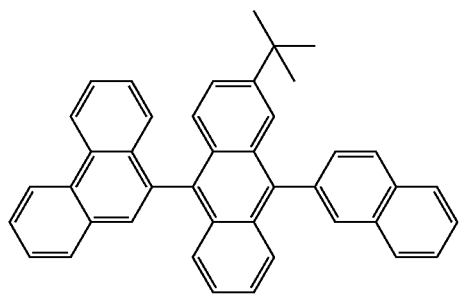
AN24
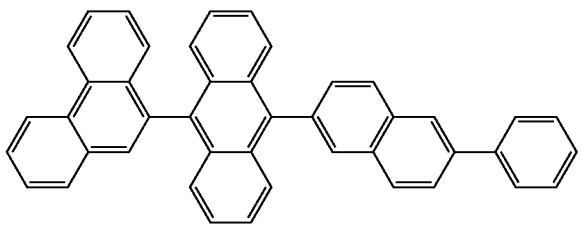

-continued
AN26
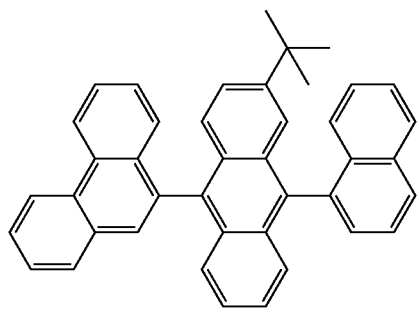
AN26
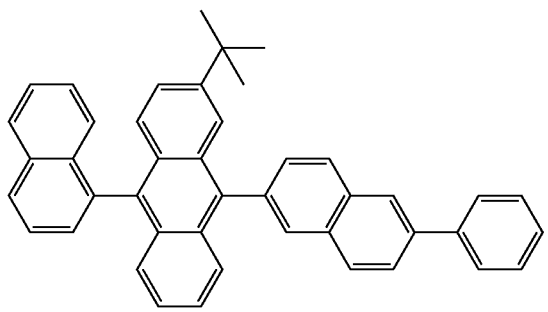
AN27
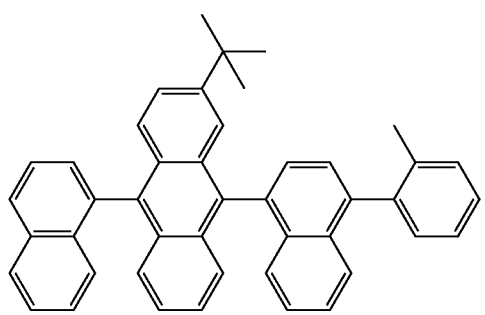
AN28
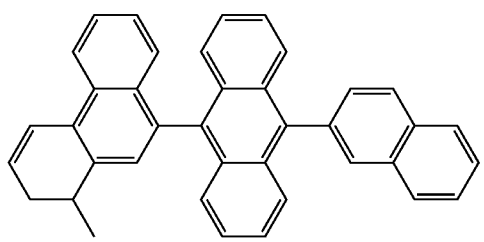
AN29
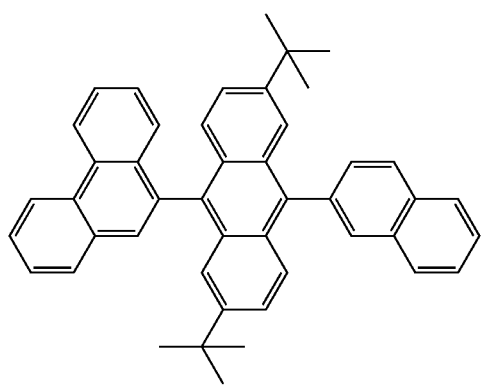
AN30
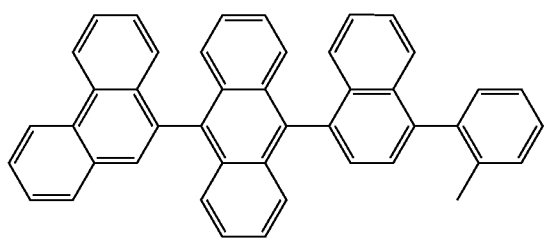
AN31
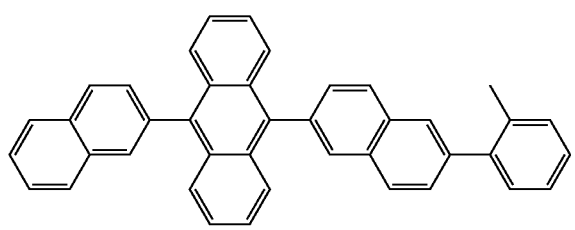
AN32
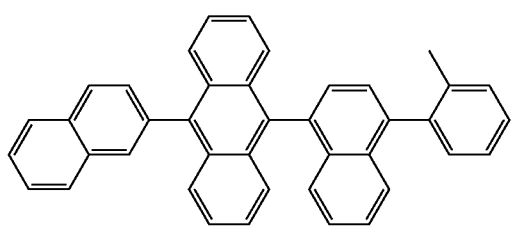
AN33
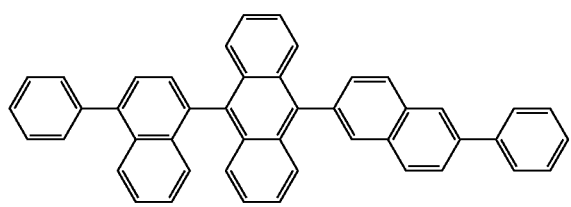
AN34
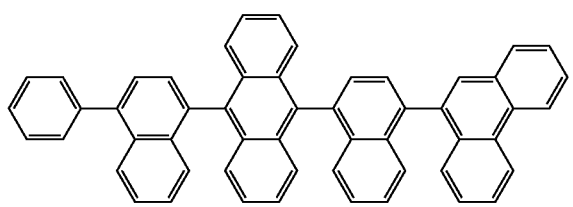

-continued
AN35
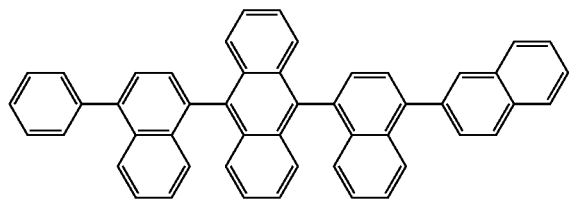
AN36
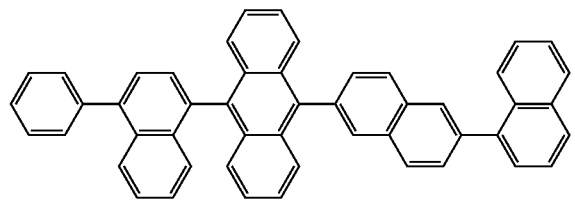
AN37
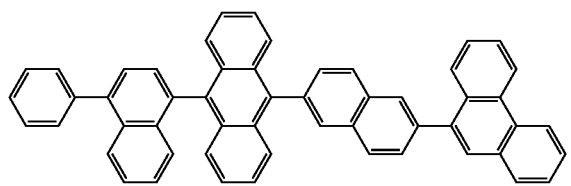
AN38
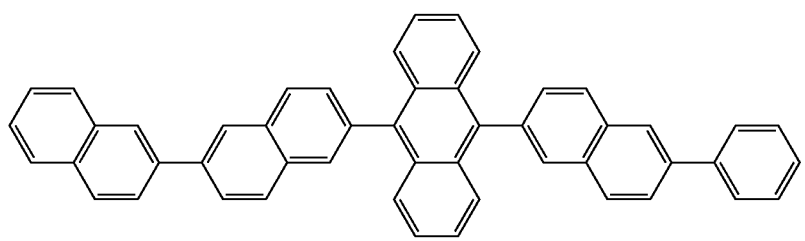
AN39
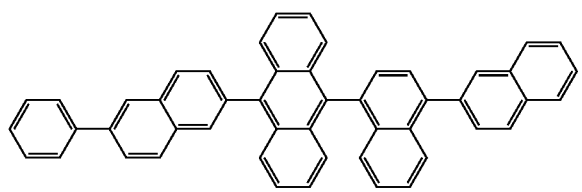
AN40
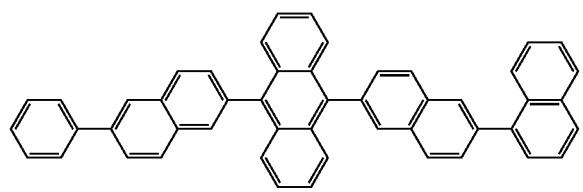
AN41
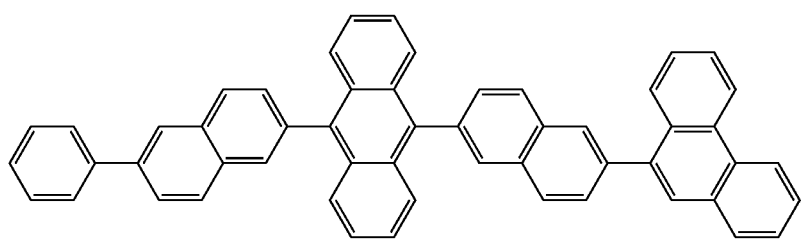
AN42
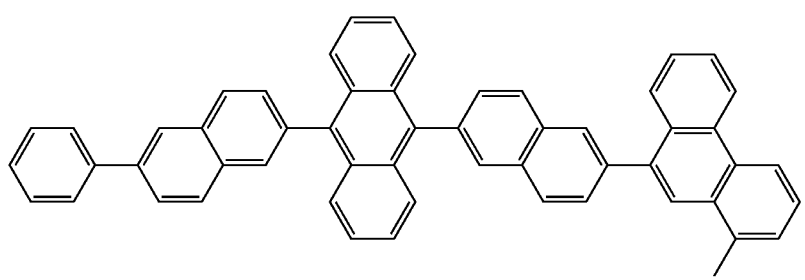

AN43
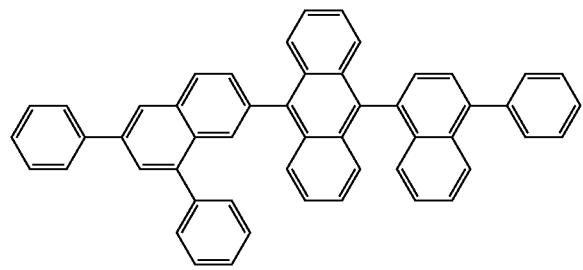

AN44
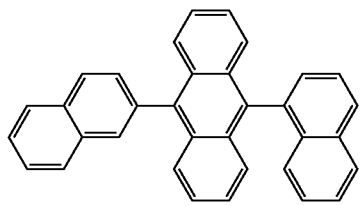

AN45
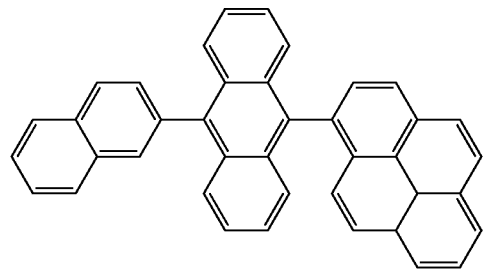

AN46
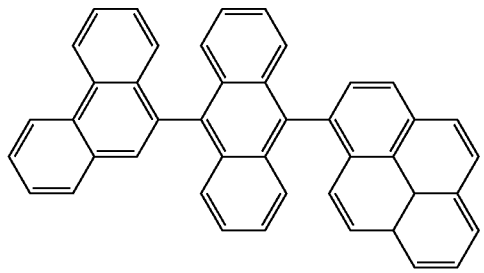

The asymmetric anthracene derivatives represented by the general formula (1) may be synthesized by using an aryl halide compound and an anthracene boronic acid compound as starting materials and applying appropriate combination of Suzuki-coupling reaction, halogenation reaction and esterification by boric acid through known methods. The following is a synthesis scheme:

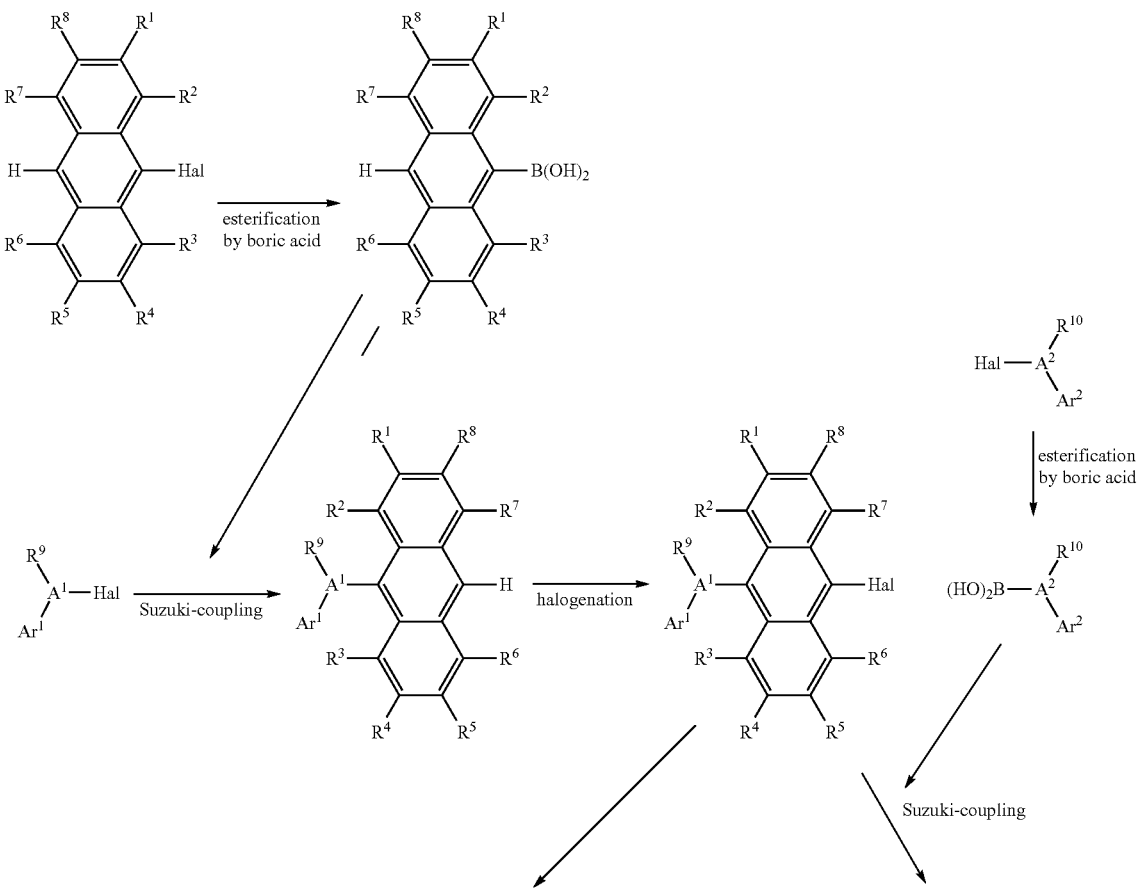

-continued

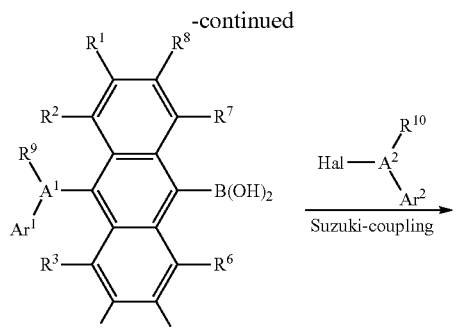
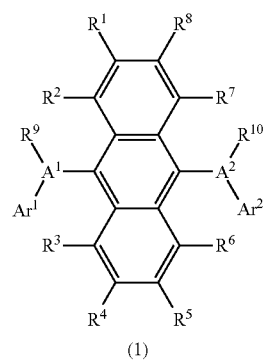

Many reports have been made on the Suzuki-coupling reaction (Chem. Rev., Vol. 95, No. 7, 2457 (1995), etc.) and the reaction conditions described in the reports may be applied. The reaction may be carried out at normal pressure or as appropriate, under pressure in inert gas atmosphere such as nitrogen, argon and helium. The reaction temperature is in the range from 15 to 300 deg C., preferably 30 to 200 deg C. The reaction solvent includes water, aromatic hydrocarbon such as benzene, toluene and xylene, ether such as 1,2-dimethoxyethane, diethylether, methyl-t-butylether, tetrahydrofuran and dioxane, saturated hydrocarbon such as pentane, hexane, heptane, octane and cyclohexane, halide such as dichloromethane, chloroform, tetrachloromethane, 1,2-dichloroethane and 1,1,1-trichloroethane, nitrile such as acetonitrile and benzonitrile, ester such as ethylacetate, methylacetate and butylacetate, and amide such as N,N-dimethylformamide, N,N-dimethylacetoamide and N-merthypyrrolidone. These solvent may used singly or as a component of mixture thereof. Among those, toluene, 1,2-dimethoxyethane, dioxane and water are preferred. Amount of the solvent to be used is generally 3 to 50 fold by weight, preferably 4 to 20 fold by weight to aryl boronic acid or derivatives thereof.

The base to be used for the reaction includes, for example, sodium carbonate, potassium carbonate, sodium hydroxide, potassium hydroxide, sodium bicarbonate, potassium bicarbonate, magnesium carbonate, lithium carbonate, potassium fluoride, cesium fluoride, cesium chloride, cesium bromide, cesium carbonate, potassium phosphate, sodium methoxide, potassium t-butoxide, sodium t-butoxide, lithium t-botoxide and the like, and sodium carbonate is preferable. Amount of the base to be used is generally 0.7 to 10 moles in equivalence, preferably 0.9 to 6 moles in equivalence to aryl boronic acid or derivatives thereof.

The catalysts to be used for the reaction include, for example, palladium catalysts such as tetrakis(triphenylphosphine)palladium, dichlorobis(triphenylphosphine)palladium, dichloro[bis(diphenylphosphono)ethane]palladium, dichloro[bis(diphenylphosphono)propane]palladium, dichloro[bis(diphenylphosphono)butane]palladium, dichloro[bis(diphenylphosphono)ferrocene]palladium and the like, nickel catalysts such as tetrakis(triphenylphosphine)nickel, dichlorobis(triphenylphosphine)nickel, dichloro[bis(diphenylphosphono)ethane]nickel, dichloro[bis(diphenylphosphono)propane]nickel, dichloro[bis(diphenylphosphono)butane]nickel, dichloro[bis(diphenylphosphono)ferrocene]nickel and the like, and tetrakis(triphenylphosphine)palladium is preferable.

Amount of the catalyst to be used is generally 0.001 to 1 mole in equivalence, preferably 0.01 to 0.1 mole in equivalence to an aryl halide compound.

Halogen for the aryl halide compounds includes, for example, an iodine atom, a bromine atom, a chlorine atom and the like, and a iodine atom and a bromine atom are preferable. Although a halogenations agent for the halogenations reaction is not limited, for example, N-halogenated chlorosuccinimide is preferably used. Amount of the halogenations agent to be used is generally 0.8 to 10 moles in equivalence, preferably 1 to 5 moles in equivalence to an aryl compound.

The reaction is generally carried out in an inert solvent under inert atmosphere such as nitrogen, argon, helium and the like.

The inert solvent to be used includes, for example, N,N-dimethylformamide, N,N-dimethylacetoamide, N-methylpyrrolidone, dimethylsulfoxide, carbon tetrachloride, chlorobenzene, dichlorobenzene, nitrobenzene, toluene, xylene, methylcellosolve, ethylcellosolve, water and the like, and N,N-dimethylformamide and N-methylpyrrolidone are preferable. Amount of the solvent to be used is generally 3 to 50 fold by weight, preferably 5 to 20 fold by weight to an aryl compound. The reaction temperature is generally in the range from 0 to 200 deg C., preferably 20 to 120 deg C.

The esterification by boric acid may be carried out in accordance with known methods (Japan Chemical Society's editorial, The Experimental Chemistry Course No. 4 edition, Vol 24, 61-90; J. Org. Chem., Vol. 60, 7508 (1995), etc.) For example, by way of lithiation or Grignard reaction of an arylhalide compound, the esterification by boric acid is carried out generally under an inert atmosphere such as nitrogen, argon, helium and by using an inert solvent as a reaction solvent. The solvents include, for example, saturated hydrocarbon such as pentane, hexane, heptane, octane and cyclohexane, ether such as 1,2-dimethoxyethane, diethylether, methyl-t-butylether, tetrahydrofuran and dioxane, aromatic hydrocarbon such as benzen, toluene and xylene. These may be used singly or as mixture thereof, and dimethylether and toluene are preferred.

Amount of the solvent to be used is generally 3 to 50 fold by weight, preferably 4 to 20 fold by weight to an arylhalide compound.

The lithiation reagent to be used includes, for example, alkyl metal reagent such as n-butyllithium, t-butyllithium, phenyllithium and methyllithium, amido-base such as lithium diisopropylamide and lithiumbistrimethylsilylamide, and n-butyllithium is preferred. Further, Grignard reagent may be prepared by reacting an arylhalide compound and a magnesium metal. Trialkyl borate to be used as esterification agent by boronic acid includes trimethyl borate, triethyl borate, triisopropyl borate, triibutyl borate and the like, and trimethyl borate and triisopropyl borate are preferred. Each amount of the lithiation reagent and a magnesium metal to be used is generally from 1 to 10 moles in equivalence, preferably from 1 to 2 moles in equivalence respectively to an arylhalide compound. Amount of trialkyl borate to be used is generally from 1 to 10 moles in equivalence, preferably from 1 to 5 moles in equivalence to an arylhalide compound (or a pyrenylhalide compound). The reaction temperature is in the range from −100 to 50° C., preferably −75 to 10 deg C.

An organic EL device of the present invention which comprises at least one organic thin film layer, which contains at least a light emitting layer, interposed between a pair of electrode consisting of an anode and a cathode, wherein the organic thin film layer comprises at least one, singly or as a component of a mixture thereof. It is preferable that the aforementioned light emitting layer comprises the aforementioned light emitting material for the organic EL device or the aforementioned material for the organic EL device singly or as a component of mixture thereof.

It is preferable that the aforementioned organic thin layer comprises the aforementioned light emitting material for the organic EL device or the aforementioned material for the organic EL device as a host material. In addition, the organic EL device of the present invention is preferred if the aforementioned light emitting layer contains further an arylamine compound and/or a styrylamine compound. The styrylamine compounds are shown by the following general formula (A):

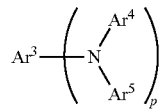
(A)

In the general formula above, $Ar^3$ represents a group selected from a phenyl group, a biphenyl group, a terphenyl group, a stilbene group and a distyryl aryl group, and $Ar^4$ and $Ar^5$ each independently represents a hydrogen atom or an aromatic hydrocarbon ring group having 6 to 20 ring carbon atoms. $Ar^3$, $Ar^4$ and $Ar^5$ each may be substituted, p represents an integer of 1 to 4, and more preferably, at least one of $Ar^4$ and $Ar^5$ is substituted with a styryl group.

In the preceding description, the aromatic hydrocarbon ring group having 6 to 20 carbon atoms includes preferably a phenyl group, a naphthyl group, an anthranil group, a phenanthryl group, a terphenyl group and the like. The preferred arylamine compounds are represented by the general formula (B):

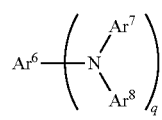
(B)

In the general formula above, $Ar^6$ to $Ar^8$ each independently represents a substituted or unsubstituted aryl group having 5 to 40 ring carbon atoms, q represents an integer of 1 to 4.

In the preceding description, the aryl group having 5 to 40 ring carbon atoms include preferably a phenyl group, a naphthyl group, an anthranil group, a phenanthryl group, a pyrenyl group, a coronyl group, a biphenyl group, a terphenyl group, a pyrrolyl group, a furanyl group, a thiophenyl group, a benzthiophenyl group, an oxadiazolyl group, a diphenylanthranil group, an indolyl group, a carbazolyl group, a pyridyl group, a benzoquinolyl group, a fluoranthenyl group, an acenaphthofluoranthenyl group, a stilbene group, a perylenyl group, a chrysenyl group, a picenyl group, a triphenylenyl group, a runicenyl group, a benzoanthracenyl group, a phenylanthranyl group, bisanthracenyl group or an aryl group represented by the following general formulae (C) and (D), and the like:

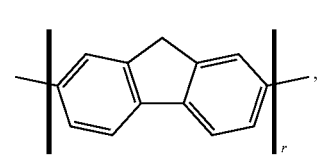
(C)

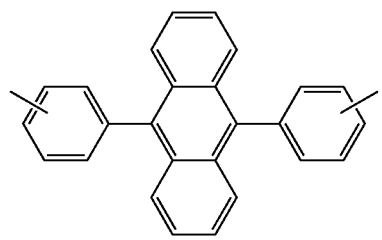
(D)

In the general formula (C), n represents an integer of 1 to 3. Additionally, preferable examples of the substituent for aforementioned aryl group include an alkyl group having 1 to 6 carbon atoms such as an ethyl group, a methyl group, an i-propyl group, a n-propyl group, a s-butyl group, a t-butyl group, a pentyl group, a hexyl group, a cyclopentyl group, a cyclohexyl group, etc., an alkoxy group having 1 to 6 carbon atoms such as an ethoxy group, a methoxy group, an i-propoxy group, a n-propoxy group, a s-butoxy group, a t-butoxy group, a pentoxy group, a hexyloxy group, a cyclopentoxy group, a cyclohexyloxy group, etc., an aryl group having 5 to 40 ring atoms, an amino group substituted with an aryl group having 5 to 40 ring atoms, an ester group which has an aryl group having 5 to 40 ring atoms, an ester group which has an alkyl group having 1 to 6 carbon atoms, a cyano group, a nitro group, a halogen atom and the like. $Ar^5$ includes preferably a naphthyl group, an anthranyl group, a chrysenyl group, a pyrenyl group or an aryl group represented by the general formula (D), of which each may be substituted.

The following is a description of the construction of the organic EL device of the present invention.

Typical examples of the construction of the organic EL device of the present invention include:

(1) an anode/a light emitting layer/a cathode;
(2) an anode/a hole injecting layer/a light emitting layer/a cathode;
(3) an anode/a light emitting layer/an electron injecting layer/a cathode;
(4) an anode/a hole injecting layer/a light emitting layer/an electron injecting layer/a cathode;
(5) an anode/an organic semiconductor layer/a light emitting layer/a cathode;

(6) an anode/an organic semiconductor layer/an electron barrier layer/a light emitting layer/a cathode;
(7) an anode/an organic semiconductor layer/a light emitting layer/an adhesion improving layer/a cathode;
(8) an anode/a hole injecting layer/a hole transporting layer/a light emitting layer/an electron injecting layer/a cathode;
(9) an anode/an insulating layer/a light emitting layer/an insulating layer/a cathode;
(10) an anode/an inorganic semiconductor layer/an insulating layer/a light emitting layer/an insulating layer/a cathode;
(11) an anode/an organic semiconductor layer/an insulating layer/a light emitting layer/an insulating layer/a cathode;
(12) an anode/an insulating layer/a hole injecting layer/a hole transporting layer/a light emitting layer/an insulating layer/a cathode; and
(13) an anode/an insulating layer/a hole injecting layer/a hole transporting layer/a light emitting layer/an electron injecting layer/a cathode.

Among those, the construction (8) is generally employed in particular; however, the construction of the organic EL device is not limited to those shown above as the examples.

In general, the organic EL device is produced on a substrate which transmits light. It is preferable that the substrate which transmits light has a transmittance of light of 50% or greater in the visible region of 400 to 700 nm. It is also preferable that a flat and smooth substrate is employed.

As the substrate which transmits light, for example, glass sheet and synthetic resin sheet are advantageously employed. Specific examples of the glass sheet include soda ash glass, glass containing barium and strontium, lead glass, aluminosilicate glass, borosilicate glass, barium borosilicate glass, quartz and the like. In addition, specific examples of the synthetic resin sheet include sheet made of polycarbonate resins, acrylic resins, polyethylene terephthalate resins, polyether sulfide resins, polysulfone resins and the like.

The anode in the organic EL device of the present invention covers a role of injecting holes into a hole transport layer or into a light emitting layer, and it is effective that the anode has a work function of 4.5 eV or greater. Specific examples of the material for the anode include indium tin oxide alloy (ITO), tin oxide (NESA), gold, silver, platinum, copper and the like.

With regard to the cathode, its material preferably has a small work function with the aim of injecting electrons into an electron transport layer or into a light emitting layer. The anode can be prepared by forming a thin film of the electrode material described above in accordance with a process such as a vapor deposition process or a sputtering process. When the light emitted from the light emitting layer is observed through the anode, it is preferable that the anode has a transmittance of the emitted light greater than 10%. It is also preferable that the sheet resistivity of the anode is several hundred Ω/☐ or smaller. The thickness of the anode is, in general, selected in the range of from 10 nm to 1 μm and preferably in the range of from 10 to 200 nm depending on a kind of the materials.

In the organic EL device of the present invention, the light emitting layer has the following functions:
(1) The injecting function: the function of injecting holes from the anode or the hole injecting layer and injecting electrons from the cathode or the electron injecting layer when an electric field is applied;
(2) The transporting function: the function of transporting injected charges (electrons and holes) by the force of the electric field; and
(3) The light emitting function: the function of providing the field for recombination of electrons and holes and leading the recombination to the emission of light.

As the process for forming the light emitting layer, a well known process such as the vapor deposition process, the spill coating process and the LB process can be employed.

It is preferable that a light emitting layer is a molecular sedimentation film particularly. Here, the molecular sedimentation film is defined as a thin film formed by sedimentation of a gas phase material compound or a thin film formed by condensation of a liquid phase material compound. The molecular sedimentation film may be differentiated from a thin film (a molecular build-up film) formed by the LB process, base on the differences between agglomeration structures and higher-order structures, and also the differences resulting from functionalities thereof. In addition, as shown in Japanese Patent Laid-open No. Showa57 (1982)-51781, to form a light emitting layer, a thin film may be formed in accordance with the spin coating and the like of the solution to be prepared by dissolving a binder such as resin and a material compound in solvent.

In the present invention, any well known light emitting material other than a light emitting material consisting of an asymmetric pyrene derivative of the present invention may be optionally contained in the light emitting layer; or a light emitting layer containing other well known light emitting layer may be laminated with the light emitting layer containing the light emitting material of the present invention each in an extent of not obstructing to achieve the objective of the present invention respectively.

In the present invention, the hole injecting layer and the hole transporting layer are layers which assist injection of holes into the light emitting layer and transport the holes to the light emitting zone. The layers exhibit a great mobility of holes and, in general, have an ionization energy as small as 5.5 eV or smaller For the hole injecting layer and the hole transporting layer, a material which transports holes to the light emitting layer at a small strength of the electric field is preferable. A material which exhibits, for example, a mobility of holes of at least $10^{-4}$ cm$^2$/V sec under application of an electric field of from $10^4$ to $10^6$ V/cm is preferable. As for such material, any arbitrary material selected from conventional material commonly used as a charge transporting material for the holes in photoconducting materials and well known material employed for the hole injecting layer in the EL device is usable.

Further examples include triazole derivatives (refer to U.S. Pat. No. 3,112,197, etc.), oxadiazole derivatives (refer to U.S. Pat. No. 3,189,447, etc.), imidazole derivatives (refer to Japanese Examined Patent KOKOKU No. Shou 37-16096, etc.), poly arylalkane derivatives (refer to U.S. Pat. Nos. 3,615,402, 3,820,989 and 3,542,544, Japanese Examined Patent KOKOKU Nos. Shou 45-555 and Shou 51-10983, Japanese Unexamined Patent Application Laid-Open Nos. Shou 51-93224, Shou 55-17105, Shou 56-4148, Shou 55-108667, Shou 55-156953, Shou 56-36656, etc.), pyrazoline derivatives and pyrazolone derivatives (refer to U.S. Pat. Nos. 3,180,729 and 4,278,746, Japanese Unexamined Application Patent Laid-Open Nos. Shou 55-88064, Shou 55-88065, Shou 49-105537, Shou 55-51086, Shou 56-80051, Shou 56-88141, Shou 57-45545, Shou 54-112637, Shou 55-74546, etc.), phenylenediamine derivatives (refer to U.S. Pat. No. 3,615,404, Japanese Examined Patent KOKOKU Nos. Shou 51-10105, Shou 46-3712 and Shou 47-25336, Japanese Unexamined Patent Application Laid-Open Nos. Shou 54-53435, Shou 54-110536, Shou 54-119925, etc.), arylamine derivatives (refer to U.S. Pat.

Nos. 3,567,450, 3,180,703, 3,240,597, 3,658,520, 4,232, 103, 4,175,961 and 4,012,376, Japanese Examined Patent KOKOKU Nos. Shou 49-35702 and Shou 39-27577, Japanese Unexamined Patent Application Laid-Open Nos. Shou 55-144250, Shou 56-119132 and Shou 56-22437, West German Patent No. 1,110,518, etc.), chalcone derivatives which is substituted with amino group (refer to U.S. Pat. No. 3,526,501, etc.), oxazole derivatives (disclosed in U.S. Pat. No. 3,257,203, etc.), styryl anthracene derivatives (refer to Japanese Unexamine Patent Application Laid-Open No. Shou 56-46234, etc.), fluorenone derivatives (refer to Japanese Unexamined Patent Application Laid-Open No. Shou 54-110837, etc.), hydrazone derivatives (refer to U.S. Pat. No. 3,717,462, Japanese Unexamined Patent Application Laid-Open Nos. Shou 54-59143, Shou 55-52063, Shou 55-52064, Shou 55-46760, Shou 55-85495, Shou 57-11350, Shou 57-148749, Hei 2-311591, etc.), stilbene derivatives (refer to Japanese Unexamined Patent Application Laid-Open Nos. Shou 61-210363, Shou 61-228451, Shou 61-14642, Shou 61-72255, Shou 62-47646, Shou 62-36674, Shou 62-10652, Shou 62-30255, Shou 60-93455, Shou 60-94462, Shou 60-174749, Shou 60-175052, etc.), silazane derivatives (U.S. Pat. No. 4,950,950), polysilane-based copolymers (Japanese Unexamined Patent Application Laid-Open No. Hei 2-204996), aniline-based copolymers (Japanese Unexamined Patent Application Laid-Open No. Hei 2-282263), an electroconductive polymer oligomer which is disclosed in Japanese Unexamined Patent Application Laid-Open No Hei 1-211399 (particularly, thiophene oligomer), etc.

With regard to the material of the hole injecting layer, the above materials are also employable, however, porphyrin compounds, aromatic tertiary amine compounds and styryl amine compounds (refer to U.S. Pat. No. 4,127,412, Japanese Unexamined Patent Application Laid-Open Nos. Shou 53-27033, Shou 54-58445, Shou 54-149634, Shou 54-64299, Shou 55-79450, Shou 55-144250, Shou 56-119132, Shou 61-295558, Shou 61-98353, Shou 63-295695, etc.) are preferable and the aromatic tertiary amine compounds are particularly preferable. Further examples include, for example, 4,4'-bis(N-(1-naphthyl)-N-phenylamino) biphenyl (abbreviated as NPD hereunder) having 2 fused aromatic rings in its molecular described in U.S. Pat. No. 5,061,569, 4,4',4''-tris(N-(3-methylphenyl)-N-phenylamino)triphenyl amine (abbreviated as MTDATA hereunder) made by connecting three triphenyl amine units to form a star burst type, etc. Further, in addition to the aforementioned aromatic dimethylidene based compounds described as a material for the light emitting layer, an inorganic compound such as p-type silicon, p-type silicon carbide or so is employable as the material for the hole injecting layer.

To form the hole injecting layer or the hole transporting layer, a thin film may be formed from the material for the hole injecting layer or the hole transporting layer, respectively, in accordance with a well known process such as the vacuum vapor deposition process, the spin coating process, the casting process and the LB process. Although the thickness of the hole injecting layer and the hole transporting layer is not particularly limited, the thickness is usually from 5 nm to 5 μm. When a hole transportation zone comprises a compound of the present invention, the hole injecting/transporting layer may be constructed by a layer consisting of at least one of the aforementioned materials, and also the hole injecting/transporting layer may be laminated by a hole injecting/transporting layer consisting of a compound different from them.

In the organic EL device of the present invention, the organic semiconductor layer assists to inject the holes or to inject the electrons into the light emitting layer, and it is preferable for the organic semiconductor layer to have a electric conductivity of $10^{-10}$ S/cm or greater. With regard to a material for the organic semiconductor layer, electroconductive oligomers such as an oligomer having thiophene, an oligomer having arylamine disclosed in Japanese Laid-Open No. Heisei 8(1996)-193191 and so on, electroconductive dendrimers such as a dendrimer having an arylamine and so on are employable.

The electron injection/transporting layer in the organic EL device of the present invention is a layer which assists injection of electrons into the light emitting layer and exhibits a great mobility of electrons. Among the electron injecting layers, an adhesion improving layer is a layer made of a material exhibiting excellent adhesion with the cathode. As the material for the electron injecting layer, 8-hydroxyquinoline, metal complexes of derivatives thereof and oxadiazole derivatives are preferable. Examples of the 8-hydroxyquinoline and metal complexes of derivatives thereof include metal chelates of oxinoid compounds including chelates of oxine (in general, 8-quinolinol or 8-hydroxyquinoline). For example, tris(8-quinolinopaluminum (Alq) can be employed as the electron injecting material. Further, examples of the oxadiazole delivertives include an electron transfer compound shown as the following general formulae:

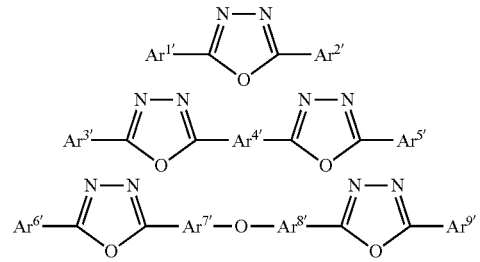

In the general formulae above $Ar^{1'}$, $Ar^{2'}$, $Ar^{3'}$, $Ar^{5'}$, $Ar^{6'}$ and $Ar^{9'}$ each independently represents a substituted or unsubstituted aryl group, which may be the same with or different from each other; $Ar^{4'}$, $Ar^{7'}$ and $Ar^{8'}$ each independently represents a substituted or unsubstituted arylene group, which may be the same with or different from each other. Examples of the aryl group include a phenyl group, a biphenyl group, an anthranil group, a perilenyl group and a pyrenyl group. Further, examples of the arylene group include a phenylene group, a naphthylene group, a biphenylene group, an anthranylene group, a perilenylene group, the pyrenylene group and the like. Furthermore, examples of the substituent include an alkyl group having 1 to 10 carbon atoms, an alkoxy group having 1 to 10 carbon atoms, a cyano group and the like. With regard to the electron transfer compound, those compounds having a thin film forming capability are preferable.

Specific examples of the electron transfer compounds are shown below:

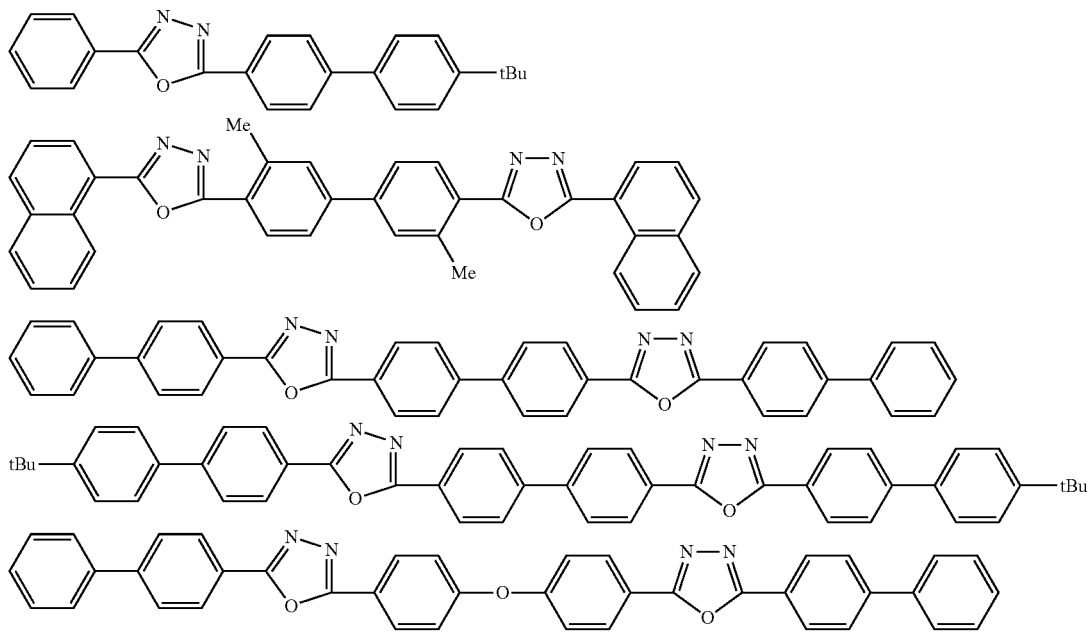

In the present invention, it is preferable that a reductive dopant is added in either the electron transporting zone or an interfacial zone between the cathode and the organic layer. The reductive dopant used in the present invention is defined as a substance which reduces the electron transporting compound. Examples of the reductive dopant include at least one compound selected from alkali metals, alkali metallic complexes, alkali metal compounds, alkaline earth metals, alkaline earth metallic complexes, alkaline earth metal compounds, rare earth metals, rare earth metallic complexes and rare earth metal compounds.

Examples of the preferable reductive dopant include at least one alkali metal selected from a group consisting of Na (the work function: 2.36 eV), K (the work function: 2.28 eV), Rb (the work function: 2.16 eV) and Cs (the work function: 1.95 eV) or at least one alkaline earth metals selected from a group consisting of Ca (the work function: 2.9 eV), Sr (the work function: 2.0 to 2.5 eV) and Ba (the work function: 2.52 eV); whose work function of 2.0 eV or less is particularly preferable. Among the above, the preferable reductive dopant include at least one alkali metal selected from a group consisting of K, Rb and Cs, the more preferred is Rb or Cs, and the most preferred is Cs. These alkali metals have particularly high ability of reduction so that improvement of an emission luminance and longer lasting of a lifetime of the organic EL device may be realized. In addition, a combination of two or more of alkali metals is also preferable as a reductive dopant having 2.9 eV or less of the work function. In particular, a combination of Cs, for example with Na, K or Rb, or Na and K is preferable. By a combing and containing Cs therein, the reduction ability can be demonstrated effectively, and improvement of an emission luminance and longer lasting of a lifetime of the organic EL device may be realized by adding it into an electron injecting area.

In the organic EL device of the present invention, an electron injecting layer formed with an insulating material or a semiconductor may be further interposed between the cathode and the organic thin film layer. The electron injecting layer effectively prevents leak in the electric current and improves the electron injecting capability. It is preferable that at least one metal compound selected from the group consisting of alkali metal chalcogenides, alkaline earth metal chalcogenides, alkali metal halides and alkaline earth metal halides is used as the insulating material. It is preferable that the electron injecting layer is constituted with the above alkali metal chalcogenides since the electron injecting property can be improved. Preferable examples of the alkali metal chalcogenides include $Li_2O$, LiO, $Na_2S$, $Na_2Se$ and NaO. Preferable examples of the alkaline earth metal chalcogenide s include CaO, BaO, SrO, BeO, BaS and CaSe.

Preferable examples of the alkali metal halides include LiF, NaF, KF, LiCl, KCl, NaCl and the like. Preferable examples of the alkaline earth metal halides include fluorides such as $CaF_2$, $BaF_2$, $SrF_2$, $MgF_2$ and $BeF_2$ and halides other than the fluorides.

Examples of the semiconductor constituting the electron transporting layer include oxides, nitrides and oxide nitrides containing at least one element selected from Ba, Ca, Sr, Yb, Al, Ga, In, Li, Na, Cd, Mg, Si, Ta, Sb and Zn, which are used singly or in combination of two or more. It is preferable that the inorganic compound constituting the electron transporting layer is in the form of a fine crystalline or amorphous insulating thin film. When the electron transporting layer is constituted with the above insulating thin film, a more uniform thin film can be formed and defective pixels such as dark spots can be decreased. Examples of the inorganic compound include the alkali metal chalcogenides, the alkaline earth metal chalcogenides, the alkali metal halides and the alkaline earth metal halides which are described above.

As the cathode for the organic EL device of the present invention, an electrode substance such as metal, alloy, electroconductive compound and those mixture having a small work function (4 eV or smaller) is employed. Examples of the electrode substance include potassium, sodium-potassium alloy, magnesium, lithium, magnesium-silver alloy, aluminum/aluminum oxide, Al/Li$_2$O, Al/LiO$_2$, Al/LiF, aluminum-lithium alloy, indium, rare earth metal and the like. The cathode can be prepared by forming a thin film of the electrode material described above in accordance with a process such as the vapor deposition process and the sputtering process. When the light emitted from the light emitting layer is observed through the cathode, it is preferable that the cathode has a transmittance of the emitted light greater than 10%. It is also preferable that the sheet resistivity of the cathode is several hundred Ω/□ or smaller. The thickness of the cathode is, in general, selected in the range of from 10 nm to 1 μm and preferably in the range of from 50 to 200 nm.

In general, an organic EL device tends to form defects in pixels due to leak and short circuit since an electric field is applied to ultra-thin films. To prevent the formation of the defects, a layer of an insulating thin film may be inserted between the pair of electrodes. Examples of the material employed for the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, vanadium oxide and the like.

Mixtures and laminates of the above compounds can also be employed.

To produce an organic EL device of the present invention, for example, a cathode, a light emitting layer and, where necessary, a hole injecting layer and an electron injecting layer are formed in accordance with the aforementioned process using the aforementioned materials, and the anode is formed in the last step. An organic EL device may be produced by forming the aforementioned layers in the order reverse to that described above, i.e., an anode being formed in the first step and a cathode in the last step. An embodiment of the process for producing an organic EL device having a construction in which a cathode, a hole injecting layer, a light emitting layer, an electron injecting layer and an anode are disposed sequentially on a light-transmitting substrate will be described in the following.

On a suitable light-transmitting substrate, a thin film made of a material for the cathode is formed in accordance with the vapor deposition process or the sputtering process so that the thickness of the formed thin film is 1 μm or smaller and preferably in the range of 10 to 200 nm. The formed thin film is employed as the cathode.

Then, a hole injecting layer is formed on the cathode. The hole injecting layer can be formed in accordance with the vacuum vapor deposition process, the spin coating process, the casting process or the LB process, as described above. The vacuum vapor deposition process is preferable since a uniform film can be easily obtained and the possibility of formation of pin holes is small. When the hole injecting layer is formed in accordance with the vacuum vapor deposition process, in general, it is preferable that the conditions in general are suitably selected in the following ranges: temperature of the deposition source: 50 to 450° C.; vacuum level: $10^{-7}$ to $10^{-3}$ Torr; deposition rate: 0.01 to 50 nm/second; temperature of the substrate: −50 to 300° C.; and film thickness: 5 nm to 5 μm; although the conditions of the vacuum vapor deposition are different depending on the employed compound (the material for the hole injecting layer) and the crystal structure and the recombination structure of the hole injecting layer to be formed.

Subsequently, the light-emitting layer is formed on the hole-injecting layer formed above. Also the formation of the light emitting layer can be made by forming the light emitting material according to the present invention into a thin film in accordance with the vacuum vapor deposition process, the sputtering process, the spin coating process or the casting process. The vacuum vapor deposition process is preferable because a uniform film can be easily obtained and the possibility of formation of pinholes is small. When the light-emitting layer is formed in accordance with the vacuum vapor deposition process, in general, the conditions of the vacuum vapor deposition process can be selected in the same ranges as those described for the vacuum vapor deposition of the hole-injecting layer although the conditions are different depending on the used compound. It is preferable that the thickness is in the range of from 10 to 40 nm.

Next, the electron-injecting layer is formed on the light-emitting layer formed above. Similarly to the hole injecting layer and the light-emitting layer, it is preferable that the electron-injecting layer is formed in accordance with the vacuum vapor deposition process since a uniform film must be obtained. The conditions of the vacuum vapor deposition can be selected in the same ranges as those for the hole injecting layer and the light-emitting layer.

In the last step, the anode is formed on the electron-injecting layer, and an organic EL device can be fabricated. The anode is made of a metal and can be formed in accordance with the vacuum vapor deposition process or the sputtering process. It is preferable that the vacuum vapor deposition process is employed in order to prevent the lower organic layers from damages during the formation of the film.

In the above production of the organic EL device, it is preferable that the above layers from the anode to the cathode are formed successively while the production system is kept in a vacuum after being evacuated. The process for forming the layers in the organic EL device of the present invention is not particularly limited. A conventional process such as the vacuum vapor deposition process and the spin coating process can be used.

The organic thin film layer comprising the compound having a spiro bond represented by the foregoing general formula (1) used in the organic EL device of the present invention can be formed in accordance with the vacuum vapor deposition process, the molecular beam epitaxy process (the MBE process) or, using a solution prepared by dissolving the compound into a solvent, in accordance with a conventional coating process such as the dipping process, the spin coating process, the casting process, the bar coating process and the roller coating process. The thickness of each layer in the organic thin film layer in the organic EL device of the present invention is not particularly limited, therefore, a thickness within the range of several nanometers to 1 μm is preferable so as to reduce the defects such as pin holes and improve the efficiency.

When a direct voltage is applied on the organic EL device produced in the above manner, when a direct voltage of 5 to 40 V is applied in the condition that the cathode is connected to a positive electrode (+) and the anode is connected to a negative electrode (−), then a light emitting is observed. When the connection is reversed, no electric current is produced and no light is emitted at all. When an alternating voltage is applied on the organic EL device, the uniform light emission is observed only in the condition that the polarity of the cathode is positive and the polarity of the anode is negative. When an alternating voltage is applied on the organic EL device, any type of wave shape can be employed.

EXAMPLE

This invention will be described in further detail with reference to Examples, which does not limit the scope of this invention.

Synthesis Example 1

Synthesis of 1-bromo-4-phenylnaphthalene 15 g of 1,4-dibromonaphthalene on the market, 7.7 g of phenylboronic acid and 1.8 g of tetrakis(triphenylphophine)palladium were mixed, followed by argon displacement. After adding 200 ml of toluene and 90 ml of 2M sodium carbonate aqueous solution thereto, it was refluxed on heating for 7 hours. After standing to cool, the organic layer was extracted by toluene, and then it was washed by water and saturated salt water. Subsequently the organic layer was dried by using sodium sulfate anhydride, and then the solvent was removed by distillation. The product was refined through a silica gel chromatography and then 8.9 g of 1-4-bromo-4-phenylnaphthalene of white crystal was obtained (Yield: 60%).

Synthesis Example 2

Synthesis of 1-bromo-4-(naphthelene-2-yl)naphthalene

The procedure of Synthesis Example 1 was repeated except that 2-naphthalene boronic acid in place of phenylboronic acid was used, and then 7.5 g of 1-bromo-4-(naphthalene-2-0 naphthalene of white crystal was obtained (yield: 43%).

Synthesis Example 3

Synthesis of 2-(biphenyl-2-yl)-6-bromonaphthelene 15 g of 2,6-dibromonaphthalene on the market, 12.5 g of 2-biphenylboronic acid and 1.8 g of tetrakis(triphenylphophine)palladium were mixed, followed by argon displacement. After adding 250 ml of toluene and 90 ml of 2M sodium carbonate aqueous solution thereto, it was refluxed on heating for 7 hours. After standing to cool, the organic layer was extracted by toluene, and then it was washed by water and saturated salt water. Subsequently the organic layer was dried by using sodium sulfate anhydride, and then the solvent was removed by distillation. The product was refined through a silica gel chromatography and then 10.9 g of 2-(biphenyl-2-yl)-6-bromonaphthalene of white crystal was obtained (yield: 58%).

Synthesis Example 4

Synthesis of 9-(naphthalene-2-yl) anthracene 22.5 g of 9-bromoanthracene, 15.8 g of 2-naphthelene boronic acid and 2.0 g of tetrakis(triphenylphophine)palladium were mixed, followed by argon displacement. After adding 150 ml of toluene and 140 ml of 2M sodiumcarbonate aqueous solution thereto, it was refluxed on heating for 7 hours. After standing to cool, the crystal precipitated was filtrated it was washed by ethanol and toluene. The crystal obtained was recrystallized in toluene, followed by filtering and drying, and then 23.1 g of 9-(naphthalene-2-yl)anthracene was obtained (yield: 87%).

Synthesis Example 5

Synthesis of 9-bromo-10-(naphthalene-2-yl)anthracene 23.1 g of 9-(naphthalene-2-yl) anthracene was dispersed into 250 ml of DMF (dimethylformamide), and then 14.9 g of NBS (N-bromosuccinimide) in DMF solution (150 ml) was dropped therein. After stirred at room temperature for 7 hours, it was left over a night. 200 ml of water was added thereto, and then the crystal precipitated was separated by filtration. Subsequently it was washed by ethanol adequately, followed by drying, and 28.8 g of 9-bromo-10-(naphthalene-2-yl)anthracene of beige color crystal was obtained (Yield: 99%).

Synthesis Example 6

Synthesis of 10-(naphthalene-2-yl)anthracene-9-boronic acid

Under argon atmosphere, 150 ml of dehydrated toluene and 150 ml of dehydrated ether were added to 28.8 g of 9-bromo-10-(naphthalene-2-yl)anthracene, and it was cooled to −63 deg C. 58 ml of 1.58M-n-butyllithium/hexane solution was dropped therein. Subsequently, it was stirred at −63 deg C. for 30 minutes, followed by heating up to −10 deg C. It was cooled to −70 deg C. again, and 23.4 ml of trimethyl boronic acid ester/dehydrated ether solution was dropped therein stepwise. After it was stirred at −70 deg C. for 2 hours, it was heated to room temperature steadily.

After left over a night, it was acidified by 10% hydrochloric aqueous solution, followed by two time extractions by toluene. The organic layer obtained was washed by saturated salt water and then dried by using sodium sulfate anhydride. After the solvent was removed by distillation, the crystal obtained was recrystallized in toluene/hexane, followed by drying, and then 17 g of 10-(naphthalene-2-yl)anthracene-9-boronic acid was obtained (yield: 65%).

Synthesis Example 7

Synthesis of 9-phenanthrene boronic acid 80 ml of dehydrated toluene and 160 ml of dehydrated THF (tetrahydrofuran) were added to 38.6 g of 9-bromophenanthrene, and was cooled to −40 deg C. After 106 ml of 1.58M n-butyllithium hexane solution was dropped, it was stirred at −40 deg C. for 30 minutes and heated to −10 deg C. It was cooled to −70 deg C. again, and 50.0 ml of trimethyl boronic acid ester/dehydrated ether solution was dropped therein stepwise. Subsequently, it was stirred at −70 deg C. for 2 hours and then heated to room temperature steadily. After left over a night, it was acidified by 10% hydrochloric aqueous solution, followed by two time extractions by toluene. The organic layer obtained was washed by saturated salt water and then dried by using sodium sulfate anhydride. After the solvent was removed by distillation, the crystal obtained was recrystallized in toluene/hexane, followed by drying, and then 21.5 g of 9-phenanthrene boronic acid of pale brown color crystal was obtained (yield: 64%).

Synthesis Example 8

Synthesis of 10-(phenanthrene-9-yl) anthracene-9-boronic acid

The procedures of Synthesis Example 4 to 6 were repeated, except that 9-phenanthrene boronic acid in place of 2-naphthalene boronic acid as the starting material was used, and then 10-(phenanthrene-9-yl)anthracene-9-boronic acid was obtained.

Production Example 1

Synthesis of AN7

5.0 g of 1-bromo-4-phenylnaphthalene, 7.38 g of 10-(naphthalene-2-yl) anthracene-9-boronic acid and 0.61 g of tetrakis(triphenylphophine)palladium were mixed, and followed by argon displacement. After adding 100 ml of DME (dimethoxyethane) and 30 ml of 2M sodium carbonate aqueous solution thereto, it was refluxed on heating for 10 hours.

After standing to cool, the crystal precipitated was filtrated, it was washed by water, methanol and then toluene. The crystal obtained was recrystallized in toluene, followed by filtering and drying, and then 6.37 g of AN7 of cream color crystal was obtained (yield: 71%).

The measurement result of the compound by FD-MS (Field Desorption Mass Spectrometry analysis) showed m/z (measured value)=506 to $C_{40}H_{26}$=506, therefore the objective compound (AN7) was confirmed.

Production Example 2

Synthesis of AN8

The procedure of Production Example 1 was repeated except that 1-bromo-4-(naphthalene-2-yl)naphthalene in place of 1-bromo-4-phenylnaphthelene was used, and then AN8 of cream color crystal was obtained (yield: 63%).

The measurement result of the compound by FD-MS showed m/z=556 to $C_{44}H_{28}$=556, therefore the objective compound (AN8) was confirmed.

Production Example 3

Synthesis of AN11

The procedure of Production Example 1 was repeated, except that 2-bromonaphthalene and 10-(phenanthrene-9-yl) anthracene-9-boronic acid in place of 1-bromo-4-phenylnaphthelene and 10-(naphthalene-2-yl) anthracene-9-boronic acid respectively were used, and then AN11 of cream color crystal was obtained (yield: 67%).

The measurement result of the compound by FD-MS showed m/z=480 to $C_{38}H_{24}$=480.

Production Example 4

Synthesis of AN13

The procedure of Production Example 1 was repeated except that 2-(biphenyl-2-yl)-6-bromonaphthalene and 10-(phenanthrene-9-yl)anthracene-9-boronic acid in place of 1-bromo-4-phenylnaphthelene and 10-(naphthalene-2-yl) anthracene-9-boronic acid respectively were used, and then AN13 of cream color crystal was obtained (yield: 67%).

The measurement result of the compound by FD-MS showed m/z=632 to $C_{50}H_{32}$=632.

Production Example 5

Synthesis of AN44

The procedure of Production Example 1 was repeated except that 1-bromonaphthelene in place of 1-bromo-4-naphthalene was used, and then AN44 of cream color crystal was obtained (yield: 69%).

The measurement result of the compound by FD-MS showed m/z=430 to $C_{34}H_{22}$=430.

Production Example 6

Synthesis of AN6

The procedure of Production Example 1 was repeated except that 2-bromo-6-phenylnaphthelene in place of 1-bromo-4-naphthalene was used, and then AN6 of cream color crystal was obtained (yield: 54%).

The measurement result of the compound by FD-MS showed m/z=506 to $C_{40}H_{26}$=506.

Production Example 7

Synthesis of AN12

The procedure of Production Example 1 was repeated except that 2-bromo-6-phenylnaphthelene and 10-(phenanthrene-9-yl)anthracene-9-boronic acid in place of 1-bromo-4-naphthalene and 10-(naphthalene-2-yl)anthracene-9-boronic acid respectively were used, and then AN13 of cream color crystal was obtained (yield; 60%).

The measurement result of the compound by FD-MS showed m/z=556 to $C_{44}H_{28}$=556.

Example 1

Fabrication of an Organic EL Device

A glass substrate (manufactured by GEOMATEC Company) of 25 mm×75 mm×1.1 mm thickness having an ITO transparent electrode was cleaned by application of ultrasonic wave in isopropyl alcohol for 5 minutes and then by exposure to ozone generated by ultraviolet light for 30 minutes. The cleaned glass substrate having an ITO transparent electrode line was fixed to a substrate holder of a vacuum deposition apparatus, and on the surface, where the ITO transparent electrode line was fixed, of the substrate, a film (hereinafter referred to as TPD232 film) having film thickness of 60 nm of the following N,N'-bis(N,N'-diphenyl-4-aminophenyl)-N,N-diphenyl-4,4'-diamino-1,1'-biphenyl was formed so as to cover the transparent electrode. The TPD232 film performs as a hole injecting layer.

Subsequently, a layer having layer thickness of 20 nm of the following N,N,N',N'-tetra(4-biphenyl)-diaminobiphenylene was formed (hereinafter referred to as TBDB layer). The layer performs as a hole transporting layer.

Subsequently, a film having a film thickness of 40 nm of the aforementioned compound AN-7 was formed as a hole transporting layer by a vapor deposition. Concurrently, as a light emitting material, the following amino compound D1 containing a styryl group was deposited at the ratio by weight between AN7 and D1 of 40:3 by a vapor deposition.

The film performs as a light emitting layer. On the film, a film having a Alq film thickness of 10 nm was formed. The film performs as an electron injecting layer.

Further, a film (film thickness: 10 inn) of Alq:Li (the source of lithium: manufactured by SAES GETTERS Company) as an electron injecting layer or a cathode was formed by binary vapor deposition of Li as a reductive dopant and the following Alq. On the Alq:Li film, Al metal was deposited to form a metal cathode; therefore, an organic EL device was fabricated.

The current efficiency of the organic EL device was measured, and also the half lifetime thereof was measured at an initial luminance of 1,000 nits. The results are shown in Table 1.

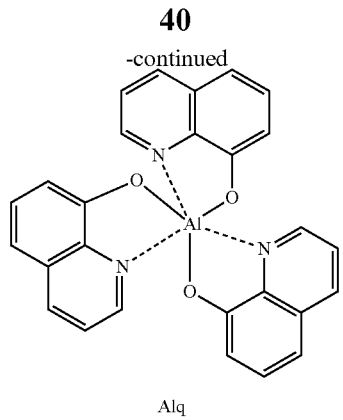

Alq

Examples 2 to 7

Fabrication of Organic EL Devices

Organic EL devices were fabricated similar to the example 1 except that the compounds described in Table 1 were used in place of the compound AN7, and then the current efficiencies and half lifetimes of the devices obtained were tested by the similar method to Example 1. The results are shown in Table 1.

Examples 8

Fabrication of Organic EL Device

Organic EL device was fabricated similar to the example 1 except that the compound AN11 in place of the compound AN7 and the amine compound D2 in place of the amine compound D1 were used as the material for the light, emitting layer, and then the current efficiency and half lifetime of the device obtained were tested by the similar method to Example 1. The results are shown in Table 1.

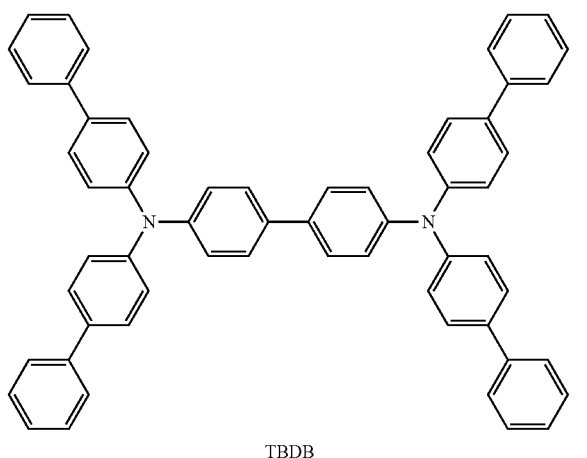

TPD232

TBDB

D1

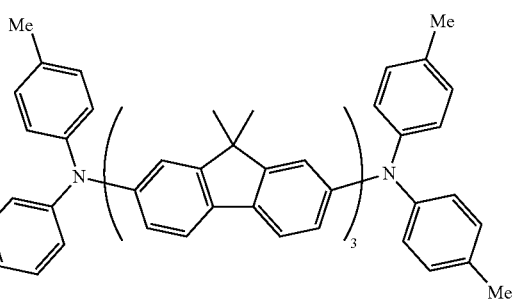

D2

Comparative Example 1

Organic EL devices were fabricated similar to the example 1 except that and was used in place of the compound AN7, and then the current efficiency and half lifetime of the device obtained was tested by the similar methods to Example 1. The results are shown in Table 1.

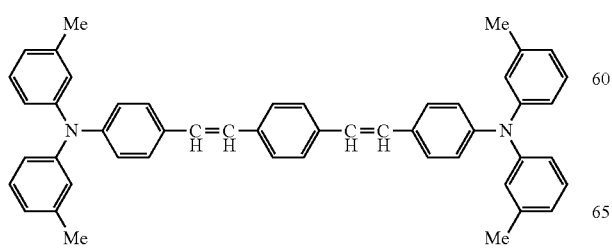

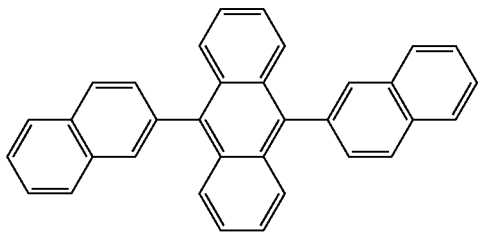

an1

TABLE 1

|  | Compound of Light-Emitting Layer | Current Efficiency (cd/A) | Half Lifetime (hours) |
| --- | --- | --- | --- |
| Example 1 | AN7/D1 | 10.9 | 4,200 |
| Example 2 | AN8/D1 | 1.3 | 4,200 |
| Example 3 | AN11/D1 | 11.0 | 5,800 |
| Example 4 | AN13/D1 | 10.8 | 3,700 |
| Example 5 | AN44/D1 | 10.0 | 3,000 |
| Example 6 | AN6/D1 | 10.1 | 3,300 |
| Example 7 | AN12/D1 | 10.8 | 4,900 |
| Example 8 | AN11/D2 | 10.3 | 3,700 |
| Comparative Example 1 | an-/D1 | 9.0 | 2,200 |

As shown in Table 1, the organic EL devices of Examples 1 to 8 exhibited a higher current efficiency and a longer lifetime than those of the device of Comparative Example 1.

What we claim is:

1. A light emitting material for an organic electroluminescent device comprising an asymmetric anthracene derivative represented by formula (1):

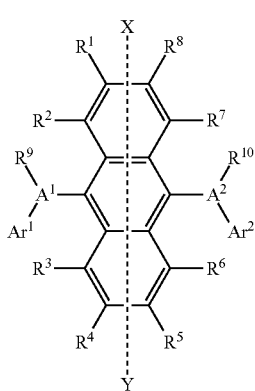

wherein
$A^1$ represents 2-naphthyl group;
$A^2$ represents 2-naphthyl group, 1-pyrenyl group, 2-pyrenyl group, or 4-pyrenyl group;
$Ar^1$ and $Ar^2$ each independently represent a hydrogen atom or a substituted or unsubstituted aromatic hydrocarbon ring group having ring carbon atoms of 6 to 50;
$R^1$ to $R^8$ each independently represent a hydrogen atom, a substituted or unsubstituted aromatic hydrocarbon ring group having ring carbon atoms of 6 to 50, a substituted or unsubstituted aromatic hetero ring group having ring atoms of 5 to 50, a substituted or unsubstituted alkyl group having carbon atoms of 1 to 50, a substituted or unsubstituted cycloalkyl group having carbon atoms of 3 to 50, a substituted or unsubstituted alkoxy group having carbon atoms of 1 to 50, a substituted or unsubstituted aralkyl group having carbon atoms of 6 to 50, a substituted or unsubstituted aryloxy group having carbon atoms of 5 to 50, a substituted or unsubstituted arylthio group having carbon atoms of 5 to 50, a substituted or unsubstituted alkoxycarbonyl group having carbon atoms of 1 to 50, a substituted or unsubstituted silyl group, a carboxyl group, a halogen atom, a cyano group, a nitro group, or a hydroxyl group;
$R^9$ to $R^{10}$ each independently represent a hydrogen atom, a substituted or unsubstituted aromatic hydrocarbon ring group having ring carbon atoms of 6 to 50, a substituted or unsubstituted alkyl group having carbon atoms of 1 to 50, a substituted or unsubstituted cycloalkyl group having carbon atoms of 3 to 50, a substituted or unsubstituted alkoxy group having carbon atoms of 1 to 50, a substituted or unsubstituted aralkyl group having carbon atoms of 6 to 50, a substituted or unsubstituted aryloxy group having carbon atoms of 5 to 50, a substituted or unsubstituted arylthio group having carbon atoms of 5 to 50, a substituted or unsubstituted alkoxycarbonyl group having carbon atoms of 1 to 50, a substituted or unsubstituted silyl group, a carboxyl group, a halogen atom, a cyano group, a nitro group, or a hydroxyl group, and none of $R^9$ and $R^{10}$ is alkenyl group;
$Ar^1$, $Ar^2$, $R^9$ and $R^{10}$ each may be a plural number, and two neighboring groups thereof may form a saturated or unsaturated ring structure;
the substituent groups at 9th and 10th positions of the anthracene at the core in formula (1) are different from each other; and
a substituent for $Ar^1$, $Ar^2$, and $R^9$ and $R^{10}$ is a halogen atom, a hydroxyl group, a nitro group, a cyano group, an alkyl group, an aryl group, a cycloalkyl group, an alkoxy group, an aralkyl group, an aryloxy group, an arylthio group, an alkoxycarbonyl group, and a carboxyl group.

2. The light emitting material for the organic electroluminescent device according to claim 1, wherein $Ar^1$ and $Ar^2$ each independently represent any one of a hydrogen atom, phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl) phenyl group, 3-methyl-2-naphthyl group, 4-methyl-1-naphthyl group, 4-methyl-1-anthryl group, 4'-methylbiphenylyl group, and 4"-t-butyl-p-terphenyl-4-yl group.

3. The light emitting material for the organic electroluminescent device according to claim 1, wherein $Ar^1$ and $Ar^2$ each independently represent any one of a hydrogen atom 1-naphthyl group, 2-naphthyl group, and 9-phenanthryl group.

4. The light emitting material for the organic electroluminescent device according to claim 1, wherein the asymmetric anthracene derivative comprises a naphtalene-1-yl group having a substituent at 4th position thereof and/or a substituted or unsubstituted condensed aromatic hydrocarbon ring group having ring carbon atoms of 12 to 20.

5. An organic electroluminescent device comprising at least one organic thin film layer which comprises a light emitting layer and which is interposed between a pair of electrode consisting of an anode and a cathode, wherein the light emitting layer comprises the light emitting material for the organic electroluminescent device according to claim 1 singly or as a component of a mixture thereof.

6. The organic electroluminescent device according to claim 5, wherein the light emitting layer comprises additionally an arylamine compound.

7. The organic electroluminescent device according to claim 5, wherein the light emitting layer comprises additionally a styrylamine compound.

8. A material for an organic electroluminescence device comprising an asymmetric anthracene derivative represented by formula (1'):

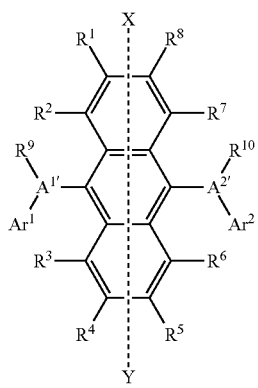

(1')

wherein, $A^{1'}$ and $A^{2'}$ each independently represent a substituted or unsubstituted condensed aromatic hydrocarbon ring group having ring carbon atoms of 10 to 20, and at least one of the groups $A^{1'}$ and $A^{2'}$ represents a naphtalene-1-yl group having a substituent at 4th position thereof or a substituted or unsubstituted condensed aromatic hydrocarbon ring group having ring carbon atoms of 12 to 20;

$Ar^1$ and $Ar^2$ each independently represent a hydrogen atom or a substituted or unsubstituted aromatic hydrocarbon ring having ring carbon atoms of 6 to 50;

$R^1$ to $R^8$ each independently represent a hydrogen atom, a substituted or unsubstituted aromatic hydrocarbon ring group having ring carbon atoms of 6 to 50, a substituted or unsubstituted aromatic hetero ring group having ring atoms of 5 to 50, a substituted or unsubstituted alkyl group having carbon atoms of 1 to 50, a substituted or unsubstituted cycloalkyl group having carbon atoms of 3 to 50, a substituted or unsubstituted alkoxy group having carbon atoms of 1 to 50, a substituted or unsubstituted aralkyl group having carbon atoms of 6 to 50, a substituted or unsubstituted aryloxy group having carbon atoms of 5 to 50, a substituted or unsubstituted arylthio group having carbon atoms of 5 to 50, a substituted or unsubstituted alkoxycarbonyl group having carbon atoms of 1 to 50, a substituted or unsubstituted silyl group, a carboxyl group, a halogen atom, a cyano group, a nitro group, or a hydroxyl group;

$R^9$ to $R^{10}$ each independently represent a hydrogen atom, a substituted or unsubstituted aromatic hydrocarbon ring group having ring carbon atoms of 6 to 50, a substituted or unsubstituted alkyl group having carbon atoms of 1 to 50, a substituted or unsubstituted cycloalkyl group having carbon atoms of 3 to 50, a substituted or unsubstituted alkoxy group having carbon atoms of 1 to 50, a substituted or unsubstituted aralkyl group having carbon atoms of 6 to 50, a substituted or unsubstituted aryloxy group having carbon atoms of 5 to 50, a substituted or unsubstituted arylthio group having carbon atoms of 5 to 50, a substituted or unsubstituted alkoxycarbonyl group having carbon atoms of 1 to 50, a substituted or unsubstituted silyl group, a carboxyl group, a halogen atom, a cyano group, a nitro group, or a hydroxyl group, and none of $R^9$ and $R^{10}$ is alkenyl group;

$Ar^1$, $Ar^2$, $R^9$ and $R^{10}$ each may be a plural number, and two neighboring groups thereof may form a saturated or unsaturated ring structure; and the substituent groups at 9th and 10th positions of the anthracene at the core in formula (1') are different from each other.

9. The light emitting material for the organic electroluminescent device according to claim 1, wherein each of $Ar^1$, $R^9$ and $R^{10}$ is a hydrogen atom, and $Ar^2$ is a substituted or unsubstituted aromatic hydrocarbon ring group having ring carbon atoms of 6 to 50.

10. The light emitting material for the organic electroluminescent device according to claim 1, wherein each of $R^9$ and $R^{10}$ is a hydrogen atom, $Ar^1$ is different from $Ar^2$, and each of $Ar^1$ and $Ar^2$ is a substituted or unsubstituted aromatic hydrocarbon ring group having ring carbon atoms of 6 to 50.

11. The light emitting material for the organic electroluminescent device according to claim 1, wherein two neighboring $R^9$'s form a saturated or unsaturated ring structure, $Ar^1$ is a hydrogen atom, $R^{10}$ is a hydrogen atom, $Ar^2$ is a substituted or unsubstituted aromatic hydrocarbon ring group having ring carbon atoms of 6 to 50.

12. The organic electroluminescent device according to claim 5, wherein the light emitting material for the organic electroluminescent device is a host material.

13. A light emitting material for an organic electroluminescent device comprising an asymmetric anthracene derivative represented by formula (1):

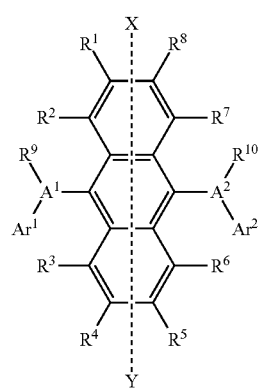

(1)

wherein

A¹ represents 1anthryl group, 2-anthryl group, or 9-anthryl group;

A² represents 1-naphthyl group, 2-naphthyl group, 1-anthryl group, 2-anthryl group, 9anthryl group, 1-phenanthryl group, 2-phenanthryl group, 3-phenanthryl group, 4-phenanthryl group, 9-phenanthryl group, 1-naphthacenyl group, 2naphthacenyl group, or 9-naphthacenyl group;

Ar¹ represents a hydrogen atom or a substituted or unsubstituted aromatic hydrocarbon ring group, wherein the aromatic hydrocarbon ring group is selected from the group consisting of phenyl group, 1-naphthyl group, 1-anthryl group, 2anthryl group, 9-anthryl group, 1phenanthryl group, 2-phenanthryl group, 3-phenanthryl group, 4-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2yl group, m-terphenyl-4-yl group, m-terphenyl-3-yl group, m-terphenyl-2-yl group, o-totyl group, m-tolyl group, p-tolyl group, p-t-butylphenyl group, p-(2-phenylpropyl) phenyl group, 3methyl-2-naphythyl group, 4-methyl-1-naphthyl group, 4-methyl-1-anthryl group, 4'-methylbiphenylyl group, and 4"-t-butyl-p-terphenyl-4-yl group;

Ar² represents a hydrogen atom or a substituted or unsubstituted aromatic hydrocarbon ring group having ring carbon atoms of 6 to 50;

R¹ to R⁸ each independently represent a hydrogen atom, a substituted or unsubstituted aromatic hydrocarbon ring group having ring carbon atoms of 6 to 50, a substituted or unsubstituted aromatic hereto ring group having ring atoms of 5 to 50, a substituted or unsubstituted alkyl group having carbon atoms of 1 to 50, a substituted or unsubstituted cycloalkyl group having carbon atoms of 3 to 50, a substituted or unsubstituted alkoxy group having carbon atoms of 1 to 50, a substituted or unsubstituted aralkyl group having carbon atoms of 6 to 50, a substituted or unsubstituted aryloxy group having carbon atoms of 5 to 50, a substituted or unsubstituted arylthio group having carbon atoms of 5 to 50, a substituted or unsubstituted alkoxycarbonyl group having carbon atoms of 1 to 50, a substituted or unsubstituted silyl group, a carboxyl group, a halogen atom, a cyano group, a nitro group, or a hydroxyl group;

R⁹ represents a hydrogen atom, a substituted or unsubstituted aromatic hydrocarbon ring group wherein the aromatic hydrocarbon ring group is selected from the group consisting of phenyl group, 1-naphthyl group, 1-anthryl group, 2-anthryl group, 9-anthryl group, 1-phenanthryl group, 2-phenanthryl group, 3-phenanthryl group, 4-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-totyl group, m-tolyl group, p-tolyl group, p-t-butylphenyl group, p-(2-phenylpropyl) phenyl group, 3methyl-2-naphythyl group, 4-methyl-1-naphthyl group, 4-methyl-1-anthryl group, 4'methylbiphenylyl group, and 4"-t-butyl-p-terphenyl-4-yl group; a substituted or unsubstituted alkyl group having carbon atoms of 1 to 50, a substituted or unsubstituted cycloalkyl group having carbon atoms of 3 to 50, a substituted or unsubstituted alkoxy group having carbon atoms of 1 to 50, a substituted or unsubstituted aralkyl group having carbon atoms of 6 to 50, a substituted or unsubstituted aryloxy group having carbon atoms of 5 to 50, a substituted or unsubstituted arylthio group having carbon atoms of 5 to 50, a substituted or unsubstituted alkoxycarbonyl group having carbon atoms of 1 to 50, a substituted or unsubstituted silyl group, a carboxyl group, a halogen atom, a cyano group, a nitro group, or a hydroxyl group;

R¹⁰ represents a hydrogen atom, a substituted or unsubstituted aromatic hydrocarbon ring group having ring carbon atoms of 6 to 50; a substituted or unsubstituted alkyl group having ring carbon atoms of 1 to 50, a substituted or unsubstituted cycloalkyl group having carbon atoms of 3 to 50, a substituted or unsubstituted cycloakyl group having carbon atoms of 3 to 50, a substituted or unsubstituted alkoxyl group having carbon atoms of 1 to 50a substituted or unsubstituted aralkyl group having carbon atoms of 6 to 50, a substituted or unsubstituted aryloxy group having carbon atoms of 5 to 50, a substituted or unsubstituted arylthio group having carbon atoms of 5 to 50, a substituted or unsubstituted alkoxycarbonyl group having carbon atoms of 1 to 50, a substituted or unsubstituted silyl group, a carboxyl group, a halogen atom, a cyano group, a nitro group, or a hydroxyl group;

and none of $R^9$ and $R^{10}$ is alkenyl group;

Ar¹, Ar², R⁹ and R¹⁰ each may be a plural number, and two neighboring groups thereof may form a aturated or unsaturated ring structure;

the substituent groups at 9th and 10th positions of the anthracene at the core in formula (1) are different from each other; and a substituent for Ar¹, Ar², R⁹ and R¹⁰ is a halogen atom, a hydroxyl group, a nitro group, a cyano group, an alkyl group, an aryl group, a cycloalkyl group, an alkoxy group, an aralkyl group, an aryloxy group, an arylthio group, an alkoxycarbonyl group, and a carboxyl group.

14. The emitting material for the organic electroluminescent device according to claim 13, wherein:

A¹ represents 1-anthryl group and A² represents 1-naphthyl group, 2-naphthyl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, or 4-pyrenyl group;

A¹ represents 2-anthryl group and A² represents 1-naphthyl group, 2-naphthyl group, 1-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, or 4-pyrenyl group; or A¹ represents 9-anthryl group and A² represents 1-naphthyl group, 2-naphthyl group, 1-anthryl group, 2-anthryl group, 1-phenanthryl group, 2-phenanthryl group, 3-phenanthryl group, 4-phenanthryl group, 9-naphthacenyl group, 1-naphthacenyl group, 2-naphthacenyl group, 9-naphthacenyl group, 1-pyrenyl group, 2-pyrenyl group, or 4-pyrenyl group.

15. The light emitting material for the organic electroluminescent device according to claim 13, wherein Ar¹ Ar² each independently represent any one of a hydrogen atom, phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4yl group, m-terphenyl-3-yl group, m-terphenyl-2-yl group, o-totyl group, m-tolyl group, p-tolyl group, p-t-butylphenyl group, p-(2-phenylpropyl) phenyl group, 3-methyl-2-naphythyl group, 4-methyl-1-naphthyl group, 4-methyl-1-anthryl group, 4'-methylbiphenylyl group, and 4"-t-butyl-p-terphenyl-4-yl group.

16. The light emitting material for the organic electroluminescent device according to claim 13, wherein $Ar^1$ $Ar^2$ each independently represent any one of a hydrogen atom, 1-naphtyl group, 2-naphtyl group, and 9-phenanthryl group.

17. The light emitting material for the organic electroluminescent device according to claim 13, wherein the asymmetric anthracene derivative comprises a naphthalene-1-yl group having a substituent at 4th position thereof and/or a substituted or unsubstituted condensed aromatic hydrocarbon ring group having ring carbon atoms of 12 to 20.

18. An organic electroluminescent device comprising at least one organic thin film layer which comprises a light emitting layer and which is interposed between a pair of electrode consisting of an anode and a cathode, wherein the light emitting layer comprises the light emitting material for the organic electroluminescent device according to claim 13 singly or as a component of a mixture thereof.

19. The organic electroluminescent device according to claim 18, wherein the light emitting material for the organic electroluminescent device is a host material.

20. The organic electroluminescent device according to claim 18, wherein the light emitting layer comprises additionally an arylamine compound.

21. The organic electroluminescent device according to claim 18, wherein the light emitting layer comprises additionally a styrylamine compound.

22. A light emitting material for an organic electroluminescent device comprising an asymmetric anthracene derivative represented by formula (1):

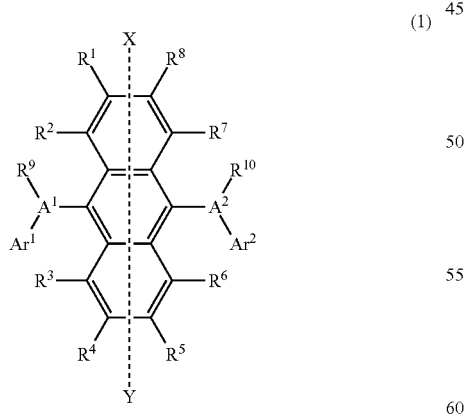

(1)

wherein
$A^1$ represents 1-pyrenyl group, 2-pyrenyl group, or 4-pyrenyl group;
$A^2$ represents 1-anthryl group, 2-anthryl group, 9-anthryl group, 1-pyrenyl group, 2-pyrenyl group, or 4-pyrenyl group;

$Ar^1$ represents a hydrogen atom or a substituted or unsubstituted aromatic hydrocarbon ring group having ring carbon atoms of 6 to 50;

$Ar^2$ represents a hydrogen atom or a substituted or unsubstituted aromatic hydrocarbon ring group, wherein the aromatic hydrocarbon ring group is selected from the group consisting of phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 2-biphenyl group, 3-biphenylyl group, 4-biphenylyl group, p-terphenyl-4-yl group, p-terphenyl-3-yl group, p-terphenyl-2-yl group, m-terphenyl-4yl group, m-terphenyl-3-yl group, m-terphenyl-2-yl group, o-tolyl group, m-tolyl group, p-tolyl group, p-t-butylphenyl group, p-(2-phenylpropyl) phenyl group, 3-methyl-2-naphythyl group, 4-methyl-1-naphthyl group, 4-methyl-1-anthryl group, 4'-methylbiphenylyl group, and 4"-t-butyl-p-terphenyl-4-yl group;

$R^1$ $R^8$ each independently represent a hydrogen atom, a substituted or unsubstituted aromatic hydrocarbon ring group having ring carbon atoms of 6 to 50, a substituted or unsubstituted aromatic hereto ring group having ring atoms of 5 to 50, a substituted or unsubstituted alkyl group having carbon atoms of 1 to 50, a substituted or unsubstituted cycloalkyl group having carbon atoms of 3 to 50, a substituted or unsubstituted alkoxy group having carbon atoms of 1 to 50, a substituted or unsubstituted aralkyl group having carbon atoms of 6 to 50, a substituted or unsubstituted aryloxy group having carbon atoms of 5 to 50, a substituted or unsubstituted arylthio group having carbon atoms of 5 to 50, a substituted or unsubstituted alkoxycarbonyl group having carbon atoms of 1 to 50, a substituted or unsubstituted silyl group, a carboxyl group, a halogen atom, a cyano group, a nitro group, or a hydroxyl group;

$R^9$ represents a hydrogen atom, a substituted or unsubstituted aromatic hydrocarbon ring group having ring carbon atoms of 6 to 50, a substituted or unsubstituted alkyl group having carbon atoms of 1 to 50, a substituted or unsubstituted cycloalkyl group having carbon atoms of 3 to 50, a substituted or unsubstituted alkoxyl group having carbon atoms of 1 to 50, a substituted or unsubstituted aralkyl group having carbon atoms of 6 to 50, a substituted or unsubstituted aryloxy group having carbon atoms of 5 to 50, a substituted or unsubstituted arylthio group having carbon atoms of 5 to 50, a substituted or unsubstituted alkoxycarbonyl group having carbon atoms of 1 to 50, a substituted or unsubstituted silyl group, a carboxyl group, a halogen atom, a cyano group, a nitro group, or a hydroxyl group;

$R^{10}$ represents a hydrogen atom or a substituted or unsubstituted aromatic hydrocarbon ring group wherein the aromatic hydrocarbon ring group is selected from the group consisting of phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 2-biphenyl group, 3-biphenylyl group, 4-biphenylyl group, p-terphenyl-4-yl group, p-terphenyl-3-yl group, p-terphenyl-2-yl group, m-terphenyl-4yl group, m-terphenyl-3-yl group, m-terphenyl-2-yl group, o-tolyl group, m-tolyl group, p-tolyl group, p-t-butylphenyl group, p-(2-phenylpropyl) phenyl group, 3methyl-2-naphythyl group, 4-methyl-1-naphthyl group, 4-methyl-1-anthryl group, 4'-methylbiphenylyl group, and 4"-t-butyl-p-terphenyl-4-yl group; a substituted or unsubstituted alkyl group having carbon atoms of 1 to 50, a substituted or unsubstituted cycloalkyl group having carbon atoms of 3 to 50, a substituted or unsubstituted alkoxy group having carbon atoms of 1 to 50, a substituted or unsubstituted aralkyl group having carbon atoms of 6 to 50, a substituted or unsubstituted aryloxy group having carbon atoms of 5 to 50, a substituted or unsubstituted arylthio group having carbon atoms of 5 to 50, a substituted or unsubstituted alkoxycarbonyl group having carbon atoms of 1 to 50, a substituted or unsubstituted silyl group a carboxyl group, a halogen atom, a cyano group, a nitro group, or a hydroxyl group;

and none of $R^9$ and $R^{10}$ is alkenyl group;

$Ar^1, Ar^2, R^9$ and $R^{10}$ each may be a plural number, and two neighboring groups thereof may form a saturated or unsaturated ring structure;

the substituent groups at 9th and 10th positions of the anthracene at the core in formula (1) are different from each other; and a substituent for $Ar^1, Ar^2, R^9$ and $R^{10}$ is a halogen atom, a hydroxyl group, a nitro group, a cyano group, an alkyl group, an aryl group, a cycloalkyl group, an alkoxy group, an aralkyl group, an aryloxy group, an arylthio group, an alkoxycarbonyl group, and a carboxyl group.

23. The light emitting material for an organic electroluminescent device according to claim 22, wherein:

$A^1$ represents 1-pyrenyl group and $A^2$ represents 1-anthryl group, 2-anthryl group, 9-anthryl group, 2-pyenyl group, or 4-pyrenyl group;

$A^1$ represents 2-pyrenyl group and $A^2$ represents 1-anthryl group, 2-anthryl group, 9-anthryl group, 1-pyrenyl group, or 4-pyrenyl group; or $A^1$ represents 4-pyrenyl group and $A^2$ represents 1-anthryl group, 2-anthryl group, 9-anthryl group, 1-pyrenyl group, or 2-pyrenyl group.

24. The light emitting material for an organic electroluminescent device according to claim 22, wherein $Ar^1$ and $Ar^2$ each independently represent any one of a hydrogen atom, phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl) phenyl group, 3-methyl-2-naphythyl group, 4-methyl-1-naphthyl group, 4-methyl-1-anthryl group, 4'-methylbiphenylyl group, and 4"-t-butyl-p-terphenyl-4-yl group.

25. The light emitting material for the organic electroluminescent device according to claim 22, wherein $Ar^1$ and $Ar^2$ each independently represent any one of a hydrogen atom, 1-naphtyl group, 2-naphtyl group, and 9-phenanthryl group.

26. The light emitting material for the organic electroluminescent device according to claim 22, wherein the asymmetric anthracene derivative comprises a naphthalene-1-yl group having a substituent at 4th position thereof and/or a substituted or unsubstituted condensed aromatic hydrocarbon ring group having ring carbon atoms of 12 to 20.

27. An organic electroluminescent device comprising at least one organic thin film layer which comprises a light emitting layer and which is interposed between a pair of electrode consisting of an anode and a cathode, wherein the light emitting layer comprises the light emitting material for the organic electroluminescent device according to claim 18 singly or as a component of a mixture thereof.

28. The organic electroluminescent device according to claim 27, wherein the light emitting material for the organic electroluminescent device is a host material.

29. The organic electroluminescent device according to claim 27, wherein the light emitting layer comprises additionally an arylamine compound.

30. The organic electroluminescent device according to claim 27, wherein the light emitting layer comprises additionally a styrylamine compound.

* * * * *